US010300145B2

(12) United States Patent
Irvine et al.

(10) Patent No.: US 10,300,145 B2
(45) Date of Patent: May 28, 2019

(54) SYNTHETIC NANOPARTICLES FOR DELIVERY OF IMMUNOMODULATORY COMPOUNDS

(71) Applicant: Massachusetts Institute of Technology, Cambridge, MA (US)

(72) Inventors: Darrell J. Irvine, Arlington, MA (US); Eric Dane, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 101 days.

(21) Appl. No.: 15/650,177

(22) Filed: Jul. 14, 2017

(65) Prior Publication Data

US 2018/0015174 A1 Jan. 18, 2018

Related U.S. Application Data

(60) Provisional application No. 62/363,064, filed on Jul. 15, 2016.

(51) Int. Cl.

| | |
|---|---|
| ***A61K 9/51*** | (2006.01) |
| ***A61K 47/64*** | (2017.01) |
| ***C07K 19/00*** | (2006.01) |
| ***C08G 69/10*** | (2006.01) |
| ***A61K 47/68*** | (2017.01) |
| ***C07K 14/00*** | (2006.01) |
| ***A61K 47/54*** | (2017.01) |
| ***A61K 47/69*** | (2017.01) |

(52) U.S. Cl.

CPC ........ *A61K 47/6425* (2017.08); *A61K 9/5123* (2013.01); *A61K 47/542* (2017.08); *A61K 47/543* (2017.08); *A61K 47/64* (2017.08); *A61K 47/645* (2017.08); *A61K 47/6807* (2017.08); *A61K 47/6911* (2017.08); *C07K 14/003* (2013.01); *C08G 69/10* (2013.01); *C07K 19/00* (2013.01)

(58) Field of Classification Search

CPC ...... A61K 9/51; A61K 9/5123; A61K 47/542; A61K 47/543; A61K 47/64; A61K 47/645; A61K 47/6807; A61K 47/6911; C07K 14/003; C07K 19/00; C08G 69/10

See application file for complete search history.

(56) References Cited

U.S. PATENT DOCUMENTS

| | | | | |
|---|---|---|---|---|
| 7,615,539 | B2 | 11/2009 | Uhlmann et al. | |
| 7,741,297 | B2 | 6/2010 | Jiang et al. | |
| 9,107,904 | B2 | 8/2015 | Irvine et al. | |
| 2003/0203359 | A1 | 10/2003 | Uhlmann et al. | |
| 2007/0104654 | A1 | 5/2007 | Hsieh et al. | |
| 2007/0154398 | A1 | 7/2007 | Wang et al. | |
| 2010/0183639 | A1 | 7/2010 | Uhlmann et al. | |
| 2011/0300163 | A1 | 12/2011 | Champion et al. | |
| 2012/0087949 | A1 | 4/2012 | Tan et al. | |
| 2012/0121606 | A1 | 5/2012 | Ruben et al. | |
| 2012/0129199 | A1 | 5/2012 | Daftarian et al. | |
| 2013/0295129 | A1* | 11/2013 | Irvine | A61K 39/0005 424/194.1 |
| 2014/0099337 | A1 | 4/2014 | Davis et al. | |
| 2014/0162944 | A1 | 6/2014 | Tiberg et al. | |
| 2014/0255378 | A1 | 9/2014 | Watkins et al. | |
| 2014/0294932 | A1 | 10/2014 | Kim et al. | |
| 2016/0333355 | A1* | 11/2016 | Deng | A61K 45/06 |

FOREIGN PATENT DOCUMENTS

| | | | |
|---|---|---|---|
| EP | 0491628 | A2 | 6/1992 |
| WO | 2004029277 | A2 | 4/2004 |
| WO | 2005117984 | A2 | 12/2005 |
| WO | 2008/043366 | A2 | 4/2008 |
| WO | WO 08/043366 | * | 4/2008 |
| WO | 2008115319 | A2 | 9/2008 |
| WO | 2008121949 | A1 | 10/2008 |
| WO | 2010071852 | A2 | 6/2010 |
| WO | 2015/112438 | A1 | 7/2015 |
| WO | WO 15/130584 | * | 9/2015 |

OTHER PUBLICATIONS

Hanson et al, J. Clin. Invest. 125(6): 2532-2546, 2015; available online May 4, 2015.*

Bachmann and Jennings, "Vaccine delivery: a matter of size, geometry, kinetics and molecular patterns" , Nat. Rev. Immunol., 10:787-96 (2010).

Ballas, et al., "Divergent therapeutic and immunologic effects of oligodeoxynucleotides with distinct CpG motifs" , J. Immunol., 167:4878-86 (2001).

Bedoui, et al., "Cross-presentation of viral and self antigens by skin-derived CD103+ dendritic cells" , Nat. Immunol., 10:488-95 (2009).

Bourqu1n, et at., "Targeting CpG oligonucleotides to the lymph node by nanoparticles elicits efficient antitumoral immunity" , J. Immunol., 181:2990-8 (2008).

Cai, et al., "Lymphatic drug delivery using engineered liposomes and solid lipid nanoparticles" , Adv. Drug Delivery Rev., 63:901-8 (2011).

Cuomo, et al., "Oligonucleotides and polynucleotides condensation onto liposome surface: effects of the base and of the nucleotide length" , Colliods Surf B Biointerfaces, 104(1):239-44 (2013).

Dane, E. et al., "Big thinking for adjuvants: Particles formed by polymeric adjuvants preferentially localize to the lymphnode and elicit robust immunity," Nature Biotechnology, vol. 33(11):1146-1148 (2015).

(Continued)

*Primary Examiner* — Kevin K Hill

(74) *Attorney, Agent, or Firm* — Nelson Mullins Riley & Scarborough LLP; Amy E. Mandragouras, Esq.; Ariana D. Harris

(57) ABSTRACT

The present disclosure provides a synthetic nanoparticle comprising a peptide nucleic acid (PNA) oligomer conjugated to a lipid, wherein the PNA oligomer noncovalently complexes with an immunomodulatory compound, thereby forming a nanoparticle. The nanoparticles are useful to elicit immune responses and can be used to treat a broad range of cancers and infectious diseases.

19 Claims, 13 Drawing Sheets
(4 of 13 Drawing Sheet(s) Filed in Color)

(56) References Cited

OTHER PUBLICATIONS

Dass, “Lipoplex-mediated delivery of nucleic acids: factors affecting in vivo transfection” , J Mol. Med., 82(9):579-91 (2004).
Davis, “G-quartets 40 years later: from 5'-GMP to molecular biology and supramolecular chemistry” , Angew. Chem. Int. Ed. Engl., 43:668-98 (2004).
Dubensky, T. et al., “Rationale, progress and development ofvaccines utilizing STING-activating cyclic dinucleotide adjuvants;” Ther Adv Vaccines, vol. 1(4) 131-143 (2013).
Hanson, M. et al., “Nanoparticulate STING agonists are potent lymph node-targeted vaccine adjuvants,” The Journal of Clinical Investigation, vol. 125 (6):2532-2546 (2015).
Hubbell, et al., “Materials engineering for immunomodulation” , Nature, 462:449-60 (2009).
Irvine, D. et al., “Engineering synthetic vaccines using cues from natural Immunity,” Nat Mater., vol. 12(11): 978-990 (2013) doi:10.1038/nmat3775.
Irvine, D. et al., “Synthetic Nanoparticles for Vaccines and Immunotherapy,” Chem Rev., vol. 115(19): 11109-11146 (2015).
Johansena, et al., “Lympho-geographical concepts in vaccine delivery” , J. Control Rel., 148:56-62 (2010).
Keler, et al., “Antibody-targeted vaccines” , Oncogene, 26:3758-67 (2007).
Klinman, “Immunotherapeutic uses of CpG oligodeoxynucleotides” , Nat. Rev. Immunol., 4:249-59 (2004).
Liu, et al., “Membrane Anchored Immunostimulatory Oligonucleotides for In Vivo Cell Modification and Localized Immunotherapy” , J. Angew, Chem., Int. Ed. (2011).
Liu, H. et al., “Guiding Principles in the Design of Molecular Bioconjugates for Vaccine Applications,” Bioconjug Chem., vol. 26(5): 791-801 (2015).
Liu, H. et al., “Structure-based Programming of Lymph Node Targeting in Molecular Vaccines,” Nature, vol. 507 (7493): 519-522 (2014) doi:10.1038/nature12978.
Manolova, et al., “Nanoparticles target distinct dendritic cell populations according to their size” , Eru. J. Immunol., 38:1404-13 (2008).
Mehta, N. et al., “Engineering New Approaches to Cancer Vaccines,” Cancer Immunol Res; 3(8): 836-843 Aug. 2015.
Mishra, et al., “Improved leishmanicidal effect of phosphorotioate antisense oligonucleotides by LDL-mediated delivery” , Biochim. Biophysica Acta, 1264 (2):229-37 (1995).
Moon, et al., “Engineering nano- and microparticles to tune immunity” , Adv. Mater., 24:3724-46 (2012).
Moyer, T. et al., “Beyond antigens and adjuvants: formulating future vaccines,” J. Clin Invest., vol. 126(3):799-808 (2016).
Dyewumi, et al., “Nano-microparticles as immune adjuvants: correlating particle sizes and the resultant immune responses” , Expert Rev. Vaccines, 9:1095-107 (2010).
Pal, et al., “The role of the lymphatic system in vaccine trafficking and immune response” , Adv. Drug Delivery Rev., 53:909-22 (2011).
Pape, et al. “The humoral immune response is initiated in lymph nodes by B cells that acquire soluble antigen directly in the follicles” , Immunity., 26:491-502 (2007).
Paramasivan, et al., “Circular dichroism of quadruplex DNAs: applications to structure, cation effects and ligand binding” , Methods 43:324-31 (2007).
Perrie, et al., “Vaccine adjuvant systems: enhancing the efficacy of sub-unit protein antigens” , Int. J. Pharm., 364:272-80 (2008).
Reddy, et al., “Exploiting lymphatic transport and complement activation innanoparticle vaccines” , Nat. Biotechnol., 25:1159-64 (2007).
Schnorrer, et al., “The dominant role of CD8+ dendritic cells in cross presentation is not dictated by antigen capture” , PNAS, 103:10729-34 (2006).
Senti, et al., “Intralymphatic immunotherapy” , Curr. Opin. Allergy Olin. Immunol., 9:537-43 (2009).
Singh, et al., “Nanoparticles and microparticles as vaccine-delivery systems” , Exp RevVaccine, 6(5):797-808 (2007).
Smith, et al., “Cutting edge: conventional CID8 alpha+ dendritic cells are preferentially involved in CTL priming after footpad infection with herpes simplex virus-1” , J. immunol., 170:4437-40 (2003).
St. John, et al., “Synthetic mast-cell granules as adjuvants to promote and polarize immunity in lymph nodes” , Nature Materials, 11:250-7 (2012).
Storhoff, et al., “Onepot colorimetric differentiation of polynucleotides with single base imperfections using gold nanoparticle probes” , J Am. Chem. Soc., 120:1959-64 (1999),.
Tacken, et al., “Dendritic-cell immunotherapy: from ex vivo loading to in vivo targeting” , Nat. Rev. Immunol., 10:790-802 (2007).
Tenbusch, et al., “Immunogenicity of DNA vaccines encoding simian immunodeficiency virus antigen targeted to dendritic cells in rhesus macaques” , PLoS ONE, 7:e39038 (2012).
Vollmer, et al., “Immunotherapeutic applications of CpG oligodeoxynucleotide TLR9 agonists” , Adv. Drug Delivery Rev., 61:195-204 (2009).
Von Beust, et al., “Improving the therapeutic index of CpG oligodeoxynucleotides by intralymphatic administration” , Eur. J. Immunol., 35:1869-76 (2005).
Wilson, et al., “Lipid-based delivery of CpG oligonucleotides enhances immunotherapeutic efficacy” , Adv. Drug Deliv. Rev., 61(3):233-42 (2009).
Zepp, “Principles of vaccine design” Lessons from nature, Vaccine, 28S:C14-C24 (2010).
Vernille, J.P., et al., “Peptide Nucleic Acid (PNA) Amphiphiles: Synthesis, Self-Assembly, and Duplex Stability,” Bioconjugate Chemistry, vol. 15(6):1314-1321 (2004).
International Search Report and Written Opinion, PCT/US2017/042139, dated Oct. 16, 2017, 15 pages.
Savard, J. et al., “Length-dependent DNA separations using multiple end-attached peptide nucleic acid amphiphiles in micellar electrokinetic chromatography,” Proteomics, vol. 29: 2779-2789 (2008).
Shen, G. et al., “Phospholipid Conjugate for Intracellular Delivery of Peptide Nucleic Acids,” Bioconjugate Chemistry, vol. 20(9):1729-1736 (2009).
Shiraishi, T. et al., “Peptide nucleic acid (PNA) cell penetrating peptide (CPP) conjugates as carriers for cellular delivery of antisense oligomers,” Artificial DNA: PNA & XN, vol. 2(3): 90-99(2011).
International Preliminary Report on Patentability, PCT/US2017/042139, dated Jan. 15, 2019, 7 pages.

* cited by examiner

1 n = 12, m = 1
2 n = 14, m = 1

3 n = 12, m = 1
4 n = 14, m = 1
5 n = 12, m = 3

6 n = 12, m = 1
7 n = 12, m = 3

8 n = 14, m = 1, R = H
9 n = 14, m = 1, R = PEG2K-maleimide

SYNTHETIC NANOPARTICLES FOR DELIVERY OF IMMUNOMODULATORY COMPOUNDS

RELATED APPLICATIONS

This application claims the benefits of the priority date of U.S. Provisional Application No. 62/363,064, which was filed on Jul. 15, 2016. The contents of this provisional application is hereby incorporated by reference in its entirety.

GOVERNMENT SUPPORT

This invention was made with Government support under Grant No. R01 EB004866 awarded by National Institutes of Health. The Government has certain rights in the invention.

BACKGROUND

The immune system plays a critical role in our health. The importance of understanding the function of the immune system and learning how to modulate immunity to protect against or treat disease and infection cannot be overstated. Compounds that can modulate both the innate immune response to fight infection and modulate the humoral and cellular response to fight cancer are needed.

Cyclic dinucleotides (CDNs) have been found to have interesting immune-stimulatory properties. CDNs have the potential to promote protective immunity through a unique pathway using the cystolic danger sensor STING (STimulator of Interferon Genes) and its downstream transcription factors. CDNs produced by bacteria elicit an innate immune response that is critical for effective host defense against infection. Additional work has shown CDNs promote cellular and humoral immunity in vaccinated mice, thus creating an interest in developing CDN-based vaccine adjuvants. Unfortunately, as small molecules, CDNs are rapidly flushed from the injection site, leading to systemic inflammatory side effects. Therefore, there remains a need for strategies for delivering CDNs based on the response desired.

SUMMARY

The present disclosure provides synthetic nanoparticles for delivery of immunomodulatory compounds, such as cyclic dinucleotides (CDNs), which have been shown to have innate immune stimulatory activity and adjuvant activity (e.g., by inducing humoral and cellular immune responses). The synthetic nanoparticles of the disclosure provide a novel delivery system for CDNs, thereby avoiding systemic inflammatory effects and allowing for efficient immune modulation.

The present disclosure is based, in part, on the discovery that a peptide nucleic acid (PNA) oligomer acts as a carrier for a cyclic dinucleotide (CDN) by forming a noncovalent complex through pi-pi base stacking and hydrogen-bonding interactions, allowing for reversible binding. In addition, the disclosure is based, in part, on the discovery that a PNA oligomer covalently conjugates to an amphiphile, as described herein, thereby forming a PNA-amphiphile conjugate which is useful to form a non-covalent complex with a CDN.

Accordingly, in one aspect, the disclosure provides a synthetic nanoparticle comprising a PNA-amphiphile conjugate and an immunomodulatory compound, wherein the PNA-amphiphile conjugate comprises (i) a peptide nucleic acid (PNA) oligomer comprising at least one guanine nucleoside, or an analog thereof, (ii) one or more lipids, and optionally, (iii) a polymer, wherein the immunomodulatory compound is a cyclic dinucleotide (CDN), and wherein the CDN is noncovalently complexed with the PNA oligomer, thereby forming a synthetic nanoparticle.

In some aspects, the PNA-amphiphile conjugate comprises a PNA oligomer comprising 3 guanine nucleosides, or analogs thereof. In some aspects, the PNA oligomer comprises at least one positively charged amino acid, e.g., lysine or arginine. In one aspect, the PNA-amphiphile conjugate comprises a PNA oligomer represented from N- to C-terminus by the formula: $Xaa_1$-$(G)_n$-$Xaa_2$, wherein $Xaa_1$ is selected from the group consisting of lysine and arginine, wherein G is guanine and n is 1 to 12, and wherein $Xaa_2$ is selected from the group consisting of lysine and arginine. In some aspects, $Xaa_1$ and $Xaa_2$ are lysine and n is 3 to 6. In some aspects, the PNA-amphiphile conjugate comprises a PNA oligomer, wherein the PNA oligomer is lysine-$(G)_3$-lysine, wherein G is guanine.

In some aspects, the disclosure provides a synthetic nanoparticle comprising a PNA-amphiphile conjugate comprising any of the PNA-oligomers described herein and one or more lipids, wherein the lipid is a diacyl lipid tail.

In some aspects, the disclosure provides a synthetic nanoparticle comprising a PNA-amphiphile conjugate comprising any of the PNA-oligomers described herein and one or more lipids, and a CDN, wherein the CDN is cyclic di-guanine mono phosphate (cdGMP). In some aspects, the synthetic nanoparticle comprises a CDN which is an agonist of STING (STimulator of Interferon Genes). In some aspects, the synthetic nanoparticle comprises a CDN which is cyclic di-inosine monophosphate or cyclic di-AMP or cyclic di-GAMP.

In some aspects, the disclosure provides a synthetic nanoparticle comprising a PNA-amphiphile conjugate comprising any of the PNA-oligomers described herein and one or more lipids, and further comprising a polymer, e.g., polyethylene glycol.

In some aspects, the disclosure provides a synthetic nanoparticle comprising a PNA-amphiphile conjugate comprising any of the PNA-oligomers described herein and one or more lipids, and a CDN, wherein the PNA oligomer is noncovalently complexed to the CDN through pi-pi base stacking and hydrogen-bonding interactions.

In some aspects, the disclosure provides a synthetic nanoparticle having a diameter in the range of approximately 10 nm to approximately 100 nm. In some aspects, the disclosure provides a synthetic nanoparticle comprising a structure selected from the group consisting of a worm-like micelle, a disc-like micelle, a nanofiber and a spherical micelle.

The disclosure also provides compositions comprising a synthetic nanoparticle as described herein, and a pharmaceutically acceptable carrier, as well as methods of modulating an immune response in a subject, comprising administering to a subject in need thereof an effective amount of the composition. Some aspects of the disclosure relate to methods of inducing or enhancing an immune response in a subject with cancer comprising administering to a subject in need thereof a composition as described herein. Some aspects of the disclosure relate to methods of treating cancer in a subject comprising administering to a subject in need thereof a composition as described herein.

The disclosure also provides methods of inhibiting a bacterial infection by administering to a subject in need thereof a composition as described herein. In some aspects, the method of inhibiting a bacterial infection comprises disrupting biofilm production.

In some aspects, the disclosure provides a vaccine comprising a synthetic nanoparticle as described herein or a composition as described herein, and an antigen, optionally wherein the antigen is conjugated to the synthetic nanoparticle. In some aspects, the vaccine is formulated for mucosal administration. In some aspects the vaccine is formulated for parenteral administration. The disclosure also provides methods of immunizing a subject by administering a vaccine as described herein.

The disclosure also provides a complex comprising a peptide nucleic acid (PNA) oligomer comprising at least one guanine nucleoside, or an analog thereof, noncovalently bound to a cyclic dinucleotide (CDN). In some aspects, the complex comprises a PNA oligomer represented from N- to C-terminus by the formula: $Xaa_1$-$(G)_n$-$Xaa_2$, wherein $Xaa_1$ is selected from the group consisting of lysine and arginine, wherein G is guanine and n is 1 to 12, and wherein $Xaa_2$ is selected from the group consisting of lysine and arginine. In some aspects, $Xaa_1$ and $Xaa_2$ are lysine and n is 3 to 6. In some aspects the PNA oligomer is lysine-$(G)_3$-lysine, wherein G is guanine. In some aspects, the CDN of the complex is cyclic di-guanine mono phosphate (cdGMP). In some aspects, the CDN of the complex is an agonist of STING (STimulator of Interferon Genes). In some aspects, the CDN of the complex is cyclic di-inosine monophosphate or cyclic d-AMP. In some aspects of the disclosure, the complex is formed by noncovalent interaction of a PNA oligomer and a CDN through pi-pi base stacking and hydrogen-bonding interactions.

The disclosure also provides a PNA-amphiphile conjugate comprising a peptide nucleic acid (PNA) oligomer comprising at least one guanine nucleoside, or an analog thereof, and one or more lipids, and optionally, a polymer conjugated to the one or more lipids or the PNA. In some aspects the PNA oligomer is represented from N- to C-terminus by the formula: $Xaa_1$-$(G)_n$-$Xaa_2$, wherein $Xaa_1$ is selected from the group consisting of lysine and arginine, wherein G is guanine and n is 1 to 12, and wherein $Xaa_2$ is selected from the group consisting of lysine and arginine. In some aspects, $Xaa_1$ and $Xaa_2$ are lysine and n is 3 to 6. In some aspects the PNA oligomer is lysine-$(G)_3$-lysine, wherein G is guanine. In some aspects, the PNA-amphiphile conjugate further comprises a cysteine chemically linked to either the N- or C-terminus of the PNA oligomer. In some aspects, the PNA-amphiphile conjugate further comprises a polymer, e.g., a polymer chemically linked via a cysteine to a PNA oligomer. In some aspects, the polymer is polyethylene glycol. In some aspects, the PNA-amphiphile conjugate comprises a structure set forth in FIG. 3.

In any of the foregoing or related aspects, the synthetic nanoparticle comprising a PNA-amphiphile conjugate and an immunomodulatory compound has slow dissociation kinetics. In some aspects, the rate of dissociation is more than one day, more than two days, or more than three days. In some aspects, the slow dissociation kinetics of the synthetic nanoparticle results in sustained release or sustained dosing of the immunomodulatory compound in a subject. In some aspects, the slow dissociation kinetics of the synthetic nanoparticle results in sustained release or sustained dosing of the immunomodulatory compound at or near the site of administration (e.g., injection site). In some aspects, the slow dissociation kinetics of the synthetic nanoparticle results in improved drug efficacy and safety, relative to the immunomodulatory compound alone.

In any of the foregoing or related aspects, the immunomodulatory compound is released from the synthetic nanoparticle comprising a PNA-amphiphile over a time span of about 6-24 hours, about 12-24 hours or about 24 hours. Accordingly, in some aspects the disclosure provides a vaccine comprising a synthetic nanoparticle as described herein, wherein a significant portion of the immunomodulatory compound is released over a period of time following administration. In some aspects, the vaccine provides release of the immunomodulatory compound in the lymphatics, where a desired immune response is achieved. In some aspects, the vaccine is administered via intradermal, subcutaneous or intramuscular injection.

In any of the foregoing or related aspects, the synthetic nanoparticle, composition or vaccine, promotes, induces or increases activation of STING. In any of the foregoing or related aspects, the synthetic nanoparticle, composition or vaccine promotes, induces or increases an antigen specific CD8+ T cell response in a subject. In any of the foregoing aspects, the synthetic nanoparticle, composition or vaccine promotes, induces or increases an immune response to a specific antigen in a subject.

In some aspects the disclosure provides methods of making a synthetic nanoparticle comprising combining a PNA-amphiphile conjugate as described herein with a cyclic dinucleotide (CDN) as described herein, thereby forming a synthetic nanoparticle. In some aspects, the synthetic nanoparticle has a diameter in the range of approximately 10 nm to approximately 100 nm. In some aspects, the synthetic nanoparticle comprises a structure selected from the group consisting of a worm-like micelle, a disc-like micelle, a nanofiber and a spherical micelle.

BRIEF DESCRIPTION OF DRAWINGS

The patent or application file contains at least one drawing executed in color. Copies of this patent or patent application publication with color drawings will be provided by the Office upon request and payment of the necessary fee.

FIG. 4A shows worm-like micelles prepared using PNA Amphiphile 2 in PBS buffer. FIG. 4B shows worm-like micelles prepared using PNA Amphiphile 4 in PBS buffer. FIG. 4C shows aggregated structures prepared using PNA Amphiphile 4 and cdGMP in PBS buffer. FIG. 4D shows lipid nanodiscs prepared using PNA Amphiphile 3 in water. FIG. 4E shows lipid nanodiscs prepared using Amphiphile 3 and cdGMP in water. FIG. 4F shows a hydrated cryopreserved sample without staining.

FIG. 6A shows the concentration bound to the PNA amphiphile as a function of the cdGMP concentration. FIG. 6B shows the fraction of soluble cdGMP bound as a function of concentration. FIG. 6C shows the release of cdGMP from the aggregates.

DETAILED DESCRIPTION

Overview

Figure 1A:
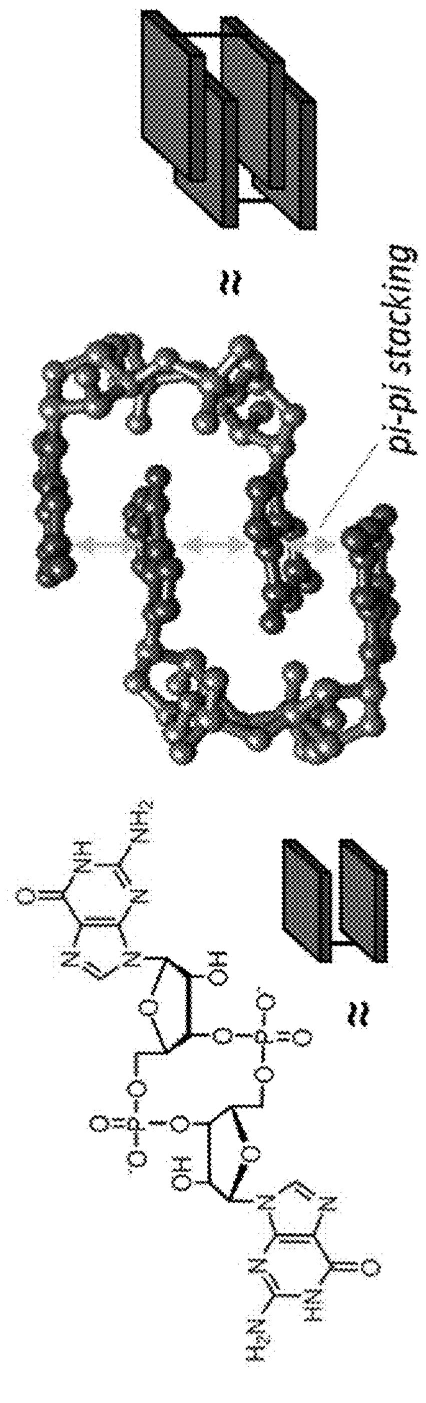
FIG. 1A depicts the chemical structure of an exemplary cyclic dinucleotide (CDN), i.e., cyclic di-GMP (cdGMP), and model of a homodimer formed in aqueous buffer, based on an X-ray crystal structure.

Modulation of the immune system is an important therapeutic strategy to treat and/or prevent a variety of diseases, such as cancer and infectious diseases. Immunomodulatory compounds, such as cyclic dinucleotides (CDNs), have the potential to modulate the immune system in a variety of ways. CDNs have both innate immune stimulation activity and adjuvant activity. However, since CDNs are small molecules, efficient delivery is problematic. CDNs are rapidly cleared from the site of injection and cause systemic inflammatory responses. Based on the present disclosure, effective delivery of CDNs to modulate the immune system is achieved by synthetic nanoparticles comprising a PNA-amphiphile conjugate reversibly complexed with a CDN.

In one aspect, the present disclosure relates to a synthetic nanoparticle comprising a PNA-amphiphile conjugate and an immunomodulatory compound, wherein the conjugate comprises a peptide nucleic acid (PNA) oligomer and one or more lipids, wherein the immunomodulatory compound is a CDN, and wherein the CDN forms a noncovalent complex with the PNA oligomer of the PNA-amphiphile conjugate. In some aspects, the PNA-amphiphile conjugate further comprises a polymer (e.g., polyethylene glycol), wherein the polymer is conjugated to a lipid or the PNA oligomer. In some aspects, the synthetic nanoparticles described herein are administered to subjects to elicit an effective immune response. In some aspects, the rate of dissociation of the immunomodulatory compound from the PNA-amphiphile is such that the synthetic nanoparticle provides sustained release or sustained dosing of the immunomodulatory compound, and improved efficacy and safety relative to the immunomodulatory compound delivered alone. In some aspects, the disclosure relates to a vaccine comprising a synthetic nanoparticle and immunomodulatory compound described herein and an antigen. In some aspects, the release profile of the immunomodulatory compound from the PNA-amphiphile is such that a vaccine described herein is suitable for intradermal, subcutaneous, or intramuscular injection, wherein the immunomodulatory compound is released over time, such as in the lymphatics, where a desired immune response is achieved. In some aspects, the vaccine promotes, induces or increases an antigen specific CD8+ T cell response in a subject. In some aspects, the vaccine promotes, induces or increases an immune response to a specific antigen in a subject. In some aspects, the present disclosure relates to methods of immunizing a subject by administering a vaccine as described herein. In another aspect, the disclosure relates to a method of treating cancer by administering a synthetic nanoparticle as described herein. In further aspects, the present disclosure relates to a method of treating a bacterial infection by administering a synthetic nanoparticle as described herein.

Definitions

Terms used in the claims and specification are defined as set forth below unless otherwise specified.

As used herein, "peptide nucleic acid" or "PNA" refers to a non-natural nucleic acid in which nucleobases are preserved while the sugar phosphate backbone is replaced with pseudo-peptide residues. A PNA maintains traditional Watson-Crick base pairing and binds strongly and with sequence selectivity to complementary DNA, RNA and PNA to form double helical structures. The term "PNA oligomer" as used herein refers to linked PNA monomers. The PNA oligomer's backbone comprises repeating N-(2-aminoethyl)-glycine units linked by peptide bonds. In certain embodiments, the linkage between consecutive PNA monomers is an amide linkage. Various purine and pyrimidine bases and non-natural bases or analogs thereof are linked to the backbone by a methylene bridge (—CH2-) and a carbonyl group (—C═O)—). A PNA oligomer is depicted like a peptide, with the N-terminus at the first (left) position and the C-terminus at the last (right) position.

As used herein, "cyclic dinucleotide" or "CDN" refers to a class of molecules comprising 2'-5' and/or 3'-5' phosphodiester linkages between two purine nucleotides. This includes 2'-5'-2',5', 2'-5'-3'5' and 3',5'-3',5' linkages. CDNs activate the cytosolic surveillance pathway through direct binding of two cytosolic pattern recognition receptors (PRRs), DEAD (aspartate-glutamate-alanine-aspartate)-box helicase 41 (DDX41) and STimulator of Interferon Genes (STING). The Type I interferon response to infection by intracellular bacteria results from the secretion of cyclic di-adenosine mono phosphate (cdAMP) or its related cyclic dinucleotide (CDN), cyclic di-guanine mono phosphate (cdGMP). CDNs bind with high affinity to DDX41, and complex with the STING adaptor protein, resulting in the activation of the TBK1/IRF3 signaling pathway, and induction of IFN-βand other IRF-3 dependent gene products that strongly activate innate immunity. CDNs are second messengers expressed by most bacteria and regulate diverse processes, including motility and formation of biofilms. Endogenous CDNs are also produced in response to cytosolic DNA by the host enzyme cyclic guanosine monophosphate-adenosine monophosphate synthase (cGAS) in tumors or during infection. In certain embodiments, a CDN is the canonical bacterial CDN, cyclic di-guanine mono phosphate (cdGMP). In certain embodiments, a CDN is the endogenous product of cGAS. In certain embodiments, a CDN is an agonist of STING.

As used herein, the term "immunomodulatory compound" refers to a compound capable of modifying or regulating one or more immune functions. In certain embodiments, an immunomodulatory compound elicits an innate immune response. In certain embodiments, an immunomodulatory compound elicits a humoral and cellular immune response. In certain embodiments, an immunomodulatory compound is an adjuvant. In certain embodiments, an immunomodulatory compound is a cyclic dinucleotide.

As used herein, the term "adjuvant" refers to a compound that, with a specific immunogen or antigen, will augment or otherwise alter or modify the resultant immune response. Modification of the immune response includes intensification or broadening the specificity of either or both antibody and cellular immune responses. Modification of the immune response can also mean decreasing or suppressing certain antigen-specific immune responses. In certain embodiments, the adjuvant is a cyclic dinucleotide.

As used herein, "amphiphile" refers to a conjugate comprising a hydrophilic head group and a hydrophobic tail, thereby forming an amphiphilic conjugate. In certain embodiments, an amphiphile comprises a conjugate comprising a hydrophilic peptide nucleic acid (PNA) oligomer head group and one or more hydrophobic lipid tails. In certain embodiments, the amphiphile further comprises a polymer (e.g., polyethylene glycol), wherein the polymer is conjugated to the one or more lipids or the PNA oligomer. In certain embodiments, an amphiphile comprises a hydrophobic lipid tail and a hydrophilic PNA oligomer head group, thereby creating an amphiphilic molecule. The amphiphiles described herein are capable of self-assembly.

As used herein, "noncovalently complexed" or "noncovalent complex" refers to the reversible association of two or more molecules. In certain embodiments, a noncovalent complex is formed through base-stacking interactions (e.g., pi-pi) and/or hydrogen-bonding. In certain embodiments, a noncovalent complex is formed between a cyclic dinucleotide and nucleobases in a peptide nucleic acid (PNA) oligomer.

As used herein, "a synthetic nanoparticle" refers to a self-assembled population of PNA-amphiphile conjugates non-covalently complexed with CDNs. In some embodiments, a nanoparticle has a diameter of less than 1000 nanometers (nm), less than 500 nm, less than 300 nm, or less than 200 nm. In some embodiments, a nanoparticle has a diameter of less than 100 nm. In some embodiments, a nanoparticle has a diameter in a range of between about 10 and 100 nm. In some embodiments, nanoparticles are micelles in that they comprise an enclosed compartment, separated from the bulk solution by a micellar membrane, comprised of amphiphilic entities which surround and enclose a space or compartment. In some embodiments, a nanoparticle has the structure of a worm-like micelle, a disk-like micelle, a nanofiber or a spherical micelle.

As used herein, "self-assembling" refers to spontaneous or induced assembly of a molecule into defined, stable, noncovalently bonded assemblies that are held together by intermolecular forces. Self-assembling molecules include protein, peptides, nucleic acids, virus-like particles, lipids and carbohydrates. In some embodiments, a PNA-amphiphile conjugate self-assembles via non-covalent interactions with an immunomodulatory compound, e.g., a CDN, to form a synthetic nanoparticle.

As used herein, "nucleobase" refers to naturally occurring heterocyclic bases such as adenine, guanine, thymine, cytosine, and uracil, and also non-naturally occurring nucleobase analogs, homologs, and modified nucleobases such as those bearing removable protecting groups.

As used herein, "vaccine" refers to a formulation which contains a synthetic nanoparticle as described herein, combined with an antigen, which is in a form that is capable of being administered to a vertebrate and which induces a protective immune response sufficient to induce immunity to prevent and/or ameliorate an infection or disease and/or to reduce at least one symptom of an infection or disease and/or to enhance the efficacy of another dose of the synthetic nanoparticle. Typically, the vaccine comprises a conventional saline or buffered aqueous solution medium in which a composition as described herein is suspended or dissolved. In this form, a composition as described herein is used to prevent, ameliorate, or otherwise treat an infection or disease. Upon introduction into a host, the vaccine provokes an immune response including, but not limited to, the production of antibodies and/or cytokines and/or the activation of cytotoxic T cells, antigen presenting cells, helper T cells, dendritic cells and/or other cellular responses.

In certain embodiments, the vaccine is a "cancer vaccine," which refers to a treatment that induces the immune system to attack cells with one or more tumor associated antigens. The vaccine can treat existing cancer (e.g., therapeutic cancer vaccine) or prevent the development of cancer in certain individuals (e.g., prophylactic cancer vaccine). The vaccine creates memory cells that will recognize tumor cells with the antigen and therefore prevent tumor growth. In certain embodiments, the cancer vaccine comprises a synthetic nanoparticle, and a tumor-associated antigen.

As used herein, the term "immunogen" or "antigen" refers to a substance such as a protein, peptide, or nucleic acid that is capable of eliciting an immune response. Both terms also encompass epitopes, and are used interchangeably.

"Amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid. Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

An "amino acid substitution" refers to the replacement of at least one existing amino acid residue in a predetermined amino acid sequence (an amino acid sequence of a starting polypeptide) with a second, different "replacement" amino acid residue. An "amino acid insertion" refers to the incorporation of at least one additional amino acid into a predetermined amino acid sequence. While the insertion will usually consist of the insertion of one or two amino acid residues, the present larger "peptide insertions," can be made, e.g. insertion of about three to about five or even up to about ten, fifteen, or twenty amino acid residues. The inserted residue(s) may be naturally occurring or non-naturally occurring as disclosed above. An "amino acid deletion" refers to the removal of at least one amino acid residue from a predetermined amino acid sequence.

"Polypeptide," "peptide", and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

"Nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer et al., *Nucleic Acid Res.* 19:5081, 1991; Ohtsuka et al., *J. Biol. Chem.* 260:2605-2608, 1985); and Cassol et al., 1992; Rossolini et al., *Mol. Cell. Probes* 8:91-98, 1994). For arginine and leucine, modifications at the second base can also be conservative. The term nucleic acid is used interchangeably with gene, cDNA, and mRNA encoded by a gene. Polynucleotides of the present invention can be composed of any polyribonucleotide or polydeoxribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, the polynucleotide can be composed of triple-stranded regions comprising RNA or DNA or both RNA and DNA. A polynucleotide can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

As used herein, the terms "linked," "fused," "conjugated," "conjugate" or "fusion," in the context of joining together of two more elements or components or domains by suitable means including chemical conjugation are used interchangeably. Methods of chemical conjugation (e.g., using heterobifunctional crosslinking agents) are known in the art.

As used herein, the term "infectious agent" refers to microorganisms that cause an infection in a vertebrate. Usually, the organisms are viruses, bacteria, parasites, protozoa and/or fungi.

As used herein, the term "antigenic formulation" or "antigenic composition" or "immunogenic composition" refers to a preparation which, when administered to a vertebrate, especially a mammal, will induce an immune response.

The term "ameliorating" refers to any therapeutically beneficial result in the treatment of a disease state, e.g., cancer, including prophylaxis, lessening in the severity or progression, remission, or cure thereof.

The term "in vivo" refers to processes that occur in a living organism.

The term "mammal" or "subject" or "patient" as used herein includes both humans and non-humans and includes, but is not limited to, humans, non-human primates, canines, felines, murines, bovines, equines, and porcines.

As used herein, "cancer antigen" refers to (i) tumor-specific antigens, (ii) tumor-associated antigens, (iii) cells that express tumor-specific antigens, (iv) cells that express tumor-associated antigens, (v) embryonic antigens on tumors, (vi) autologous tumor cells, (vii) tumor-specific membrane antigens, (viii) tumor-associated membrane antigens, (ix) growth factor receptors, (x) growth factor ligands, and (xi) any other type of antigen or antigen-presenting cell or material that is associated with a cancer.

The term "sufficient amount" or "amount sufficient to" means an amount sufficient to produce a desired effect, e.g., an amount sufficient to reduce the diameter of a tumor.

The term "therapeutically effective amount" is an amount that is effective to ameliorate a symptom of a disease. A therapeutically effective amount can be a "prophylactically effective amount" as prophylaxis can be considered therapy.

As used herein, "immune cell" is a cell of hematopoietic origin and that plays a role in the immune response. Immune cells include lymphocytes (e.g., B cells and T cells), natural killer cells, and myeloid cells (e.g., monocytes, macrophages, eosinophils, mast cells, basophils, and granulocytes).

The term "T cell" refers to a CD4+ T cell or a CD8+ T cell. The term T cell encompasses TH1 cells, TH2 cells and TH17 cells.

The term "T cell cytotoxicity" includes any immune response that is mediated by CD8+ T cell activation. Exemplary immune responses include cytokine production, CD8+ T cell proliferation, granzyme or perforin production, and clearance of an infectious agent.

As generally used herein, "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

As used herein, "about" will be understood by persons of ordinary skill and will vary to some extent depending on the context in which it is used. If there are uses of the term which are not clear to persons of ordinary skill given the context in which it is used, "about" will mean up to plus or minus 10% of the particular value.

It must be noted that, as used in the specification and the appended claims, the singular forms "a," "an" and "the" include plural referents unless the context clearly dictates otherwise.

Compositions of Synthetic Nanoparticles

A synthetic nanoparticle as described herein comprises a PNA-amphiphile conjugate non-covalently complexed with a CDN. The PNA-amphiphile conjugate comprises a PNA oligomer conjugated to one or more lipids, and optionally one or more polymers.

A. Peptide Nucleic Acid (PNA) Oligomer

PNAs are compounds that in some respects are analogous to oligonucleotides, but which differ in structure. In peptide nucleic acids, the deoxyribose backbone of an oligonucleotide has been replaced with a backbone having peptide linkages. Each subunit has attached a naturally occurring or non-naturally occurring base. One such backbone is constructed of repeating units of N-(2-aminoethyl)glycine linked through amide bonds.

PNA binds both DNA and RNA to form PNA/DNA or PNA/RNA duplexes. The resulting PNA/DNA or PNA/RNA duplexes are bound with greater affinity than corresponding DNA/DNA or DNA/RNA duplexes as evidence by their higher melting temperatures ($T_m$). This high thermal stability has been attributed to the neutrality of the PNA backbone, which does not encounter the charge repulsion present in DNA or RNA duplexes. The neutral backbone of the PNA also renders the $T_m$s of PNA/DNA(RNA) duplexes practically independent of salt concentration. Thus the PNA/DNA duplex offers a further advantage over DNA/DNA duplex interactions which are highly dependent on ionic strength.

In addition to increased affinity, PNA has also been shown to bind to DNA with increased specificity. When a PNA/DNA duplex mismatch is melted relative to the DNA/DNA duplex there is an 8 to 20° C. drop in the $T_m$. This magnitude of a drop in $T_m$ is not seen with the corresponding DNA/DNA duplex with a mismatch present, See Egholm, M., et al., *Nature* 1993 365 p. 566.

The binding of a PNA strand to a DNA or RNA strand can occur in one of two orientations. The orientation is said to be anti-parallel when the DNA or RNA strand in a 5' to 3' orientation binds to the complementary PNA strand such that the carboxyl end of the PNA is directed towards the 5' end of the DNA or RNA and amino end of the PNA is directed towards the 3' end of the DNA or RNA. In the parallel orientation the carboxyl end and amino end of the PNA are in reverse orientation with respect to the 5'-3' direction of the DNA or RNA.

A further advantage of PNA compared to oligonucleotides is that their polyamide backbone is not recognized by either nucleases or proteases, and are therefore resistant to degradation by enzymes.

PNA oligomers suitable for use in the present disclosure are described, for example, in U.S. Pat. Nos. 5,539,082 and 7,223,833; and WO 92/20702, each hereby incorporated by reference.

In certain embodiments, a PNA oligomer comprises a cysteine, thereby introducing a free thiol to allow for further conjugation reactions.

In certain embodiments, a PNA oligomer comprises at least one nucleobase. In certain embodiments, the at least one nucleobase is naturally occurring. In certain embodiments, the at least one nucleobase is a non-naturally occurring nucleobase analog, homolog, or modified nucleobase. In certain embodiments, a PNA oligomer comprises at least one guanine nucleoside, or an analog thereof. In certain embodiments, a PNA oligomer comprises one to twelve guanine nucleosides, or analogs thereof. In certain embodiments, a PNA oligomer comprises up to fifteen guanine nucleosides, or analogs thereof. In certain embodiments, a PNA oligomer comprises three guanine nucleosides, or analogs thereof. In certain embodiments, a PNA oligomer comprises five guanine nucleosides, or analogs thereof. In certain embodiments, the number of guanine nucleosides present in a PNA oligomer determines the structure of a synthetic nanoparticle. For example, a higher number of guanine nucleosides, or analogs thereof, results in a nanofiber structure. In certain embodiments, a PNA oligomer comprises at least one guanine nucleoside, or an analog thereof, to form a noncovalent bond with a cyclic dinucleotide (CDN).

In some embodiments, a PNA oligomer comprises at least one positively charged amino acid. In some embodiments, a PNA oligomer comprises two positively charged amino acids, at least 3, at least 4, at least 5, at least 6, at least 7, at least 8, at least 9 or at least 10 positively charged amino acids. In some embodiments, at least one positively charged amino acid is on the N-terminus of a PNA oligomer and at least one positively charged amino add is on the C-terminus of a PNA oligomer, or both. In some embodiments, a PNA oligomer comprises at least one lysine at the N- and C-terminus of the PNA oligomer. In certain embodiments, a PNA oligomer comprises at least two lysines at the N- and C-terminus of the PNA. oligomer. In some embodiments, a PNA oligomer comprises at least one arginine. In some embodiments, a PNA oligomer comprises two arginines. In some embodiments, at least one positively charged amino acid is included in the PNA oligomer to increase solubility of the amphiphile-adjuvant, described herein. In some embodiments, a PNA oligomer includes two positively charged amino acids (e.g., lysine) regardless of the number of guanine nucleosides, or analogs thereof.

In some embodiments, a PNA oligomer is represented by the formula: $Xaa_1$-$(NB)_n$-$Xaa_2$, wherein "NB" refers to nucleobase. In some embodiments, a PNA oligomer is represented by the following formula: $(Xaa_1)_m$-$(NB)_n$-$(Xaa_2)_p$, wherein "NB" refers to any nucleobase, or analog thereof, n is 1-20, Xaa1 and Xaa2 are any amino acid, and m=1-20 and p=1-20. In some embodiments, a PNA oligomer is represented by the formula: $(Xaa_1)_m$-$(G)_n$-$(Xaa_2)_p$, wherein "G" is a guanine nucleobase, or analog thereof, n=1-12, Xaa1 and Xaa2 are any amino acid, and m=1-12 and p=1-12. In some embodiments, a PNA oligomer is represented by the formula: $(Xaa_1)_m$-$(G)_n$-$(Xaa_2)_p$, wherein "G" is a guanine nucleobase, or analog thereof, n=1-6, Xaa1 and Xaa2 are positively charged amino acids, and m=1-6 and p=1-6. In some embodiments, a PNA oligomer is represented by the formula: $Xaa_1$-$(G)_n$-$Xaa_2$, wherein "G" is a guanine nucleobase, or analog thereof, n=1-12, and Xaa1 and Xaa2 are positively charged amino acids. In some embodiments, a PNA oligomer is represented by the formula: $Xaa_1$-$(G)_n$-$Xaa_2$, wherein "G" is a guanine nucleobase, or analog thereof, n=1-6, and Xaa1 and Xaa2 are positively charged amino acids. In some embodiments, $Xaa_1$ and $Xaa_2$ are both positively charged amino acids. In certain embodiments $Xaa_1$ and $Xaa_2$ are different, positively charged amino acids. In certain embodiments $Xaa_1$ and $Xaa_2$ are the same, positively charged amino acid. In certain embodiments, $Xaa_1$ and $Xaa_2$ are lysine. In certain embodiments, $Xaa_1$ and $Xaa_2$ are arginine. In certain embodiments, n=1-12. In certain embodiments n=3. In certain embodiments, m=1-12. In certain embodiments, p=1-12. In certain embodiments, m=1, n=3, and p=1. In certain embodiments, m=1, n=5, and p=1.

B. Amphiphile (i) Lipid Component

An amphiphile typically includes a hydrophobic lipid. The lipid can be linear, branched, or cyclic. In certain embodiments, the lipid binds albumin, allowing for trafficking to the lymph nodes. In certain embodiments, the lipid is at least 17 to 18 carbons in length, but may be shorter if it shows good albumin binding and adequate targeting to the lymph nodes. In certain embodiments, amphiphiles include lipid-oligonucleotide conjugates and lipid-peptide conjugates that can be trafficked from the site of delivery through the lymph to the lymph node. In certain embodiments, the activity relies, in-part, on the ability of the conjugate to associate with albumin in the blood of the subject. Therefore, in certain embodiments, amphiphiles include a lipid that can bind to albumin under physiological conditions. Lipids suitable for targeting the lymph node can be selected based on the ability of the lipid or a lipid conjugate including the lipid to bind to albumin. Suitable methods for testing the ability of the lipid or lipid conjugate to bind to albumin are known in the art.

For example, in certain embodiments, a plurality of amphiphiles is allowed to spontaneously form micelles in aqueous solution. The micelles are incubated with albumin, or a solution including albumin such as Fetal Bovine Serum (FBS). Samples can be analyzed, for example, by ELISA, diameter exclusion chromatography or other methods to determine if binding has occurred. Amphiphiles can be selected as lymph node-targeting conjugates if in the presence of albumin, or a solution including albumin such as Fetal Bovine Serum (FBS), the micelles dissociate and the amphiphiles bind to albumin as discussed above.

Examples of preferred lipids for use in lymph node targeting amphiphiles include, but are not limited to, fatty acids with aliphatic tails of 8-30 carbons including, but not limited to, linear unsaturated and saturated fatty acids, branched saturated and unsaturated fatty acids, and fatty acids derivatives, such as fatty acid esters, fatty acid amides, and fatty acid thioesters, diacyl lipids, cholesterol, cholesterol derivatives, and steroid acids such as bile acids, Lipid A or combinations thereof.

In certain embodiments, the lipid is a diacyl lipid or two-tailed lipid. In some embodiments, the tails in the diacyl lipid contain from about 8 to about 30 carbons and can be saturated, unsaturated, or combinations thereof. The tails can be coupled to the head group via ester bond linkages, amide bond linkages, thioester bond linkages, or combinations thereof. In a particular embodiment, the diacyl lipids are phosphate lipids, glycolipids, sphingolipids, or combinations thereof.

Preferably, lymph node-targeting amphiphiles include a lipid that is 8 or more carbon units in length. It is believed that increasing the number of lipid units can reduce insertion of the lipid into plasma membrane of cells, allowing the lipid conjugate to remain free to bind albumin and traffic to the lymph node.

For example, the lipid can be a diacyl lipid composed of two C18 hydrocarbon tails. In certain embodiments, the lipid for use in preparing lymph node targeting lipid conjugates is not a single chain hydrocarbon (e.g., C18), or cholesterol. Cholesterol conjugation has been explored to enhance the immunomodulation of molecular adjuvants and immunogenicity of peptides, but cholesterol conjugates, which associate well with lipoproteins but poorly with albumin, show poor lymph node targeting and low immunogenicity in vaccines compared to optimal albumin-binding conjugates.

(ii) Polymers

In certain embodiments, an amphiphile comprises a polymer. In certain embodiments, a polymer increases solubility of an amphiphile or nanoparticle.

For the amphiphile or nanoparticle to be trafficked efficiently, the conjugate should remain soluble. Therefore, in certain embodiments, a polymer is included in the amphiphile or nanoparticle to increase solubility. The polymer reduces or prevents the ability of the lipid to insert into the plasma membrane of cells, such as cells in the tissue adjacent to the injection site. The polymer can also reduce or prevent the ability of the amphiphile from non-specifically associating with extracellular matrix proteins at the site of administration. The length and composition of the polymer can be adjusted based on the lipid selected.

A polymer can be used as part of any of an amphiphile or nanoparticle suitable for use in the methods disclosed herein. Suitable polymers include, but are not limited to, a hydrophilic polymer including but not limited to poly(ethylene glycol) (MW: 500 Da to 20,000 Da), polyacrylamide (MW: 500 Da to 20,000 Da), polyacrylic acid; a string of hydrophilic amino acids such as serine, threonine, cysteine, tyrosine, asparagine, glutamine, aspartic acid, glutamic acid, lysine, arginine, histidine, or combinations thereof polysaccharides, including but not limited to, dextran (MW: 1,000 Da to 2,000,000 Da), or combinations thereof.

In certain embodiments, the polymer is one or more ethylene glycol (EG) units, more preferably two or more EG units (i.e., polyethylene glycol (PEG)). For example, in certain embodiments, a peptide nucleic acid (PNA) oligomer and a hydrophobic lipid are linked by a polyethylene glycol (PEG) molecule or a derivative or analog thereof. In other embodiments, a polymer is conjugated to a hydrophobic lipid, with or without a linker.

In certain embodiments, amphiphiles suitable for use in the methods disclosed herein contain a PNA oligomer linked to PEG which is in turn linked to a hydrophobic lipid, either covalently or via formation of amphiphiles that hybridize to micelles. The precise number of EG units depends on the lipid and the PNA oligomer, however, typically, a polymer can have between about 1 and about 100, between about 20 and about 80, between about 30 and about 70, or between about 40 and about 60 EG units. In certain embodiments, the polymer has between about 45 and 55 EG, units. For example, in certain embodiments, the polymer has 48 EG units. In certain embodiments, the polymer has 42+/−EG units.

Determination of the number of EG units can readily be determined using the methods known in the art. For example, in certain embodiments, the number of EG units is determined using mass spectrometry. In certain embodiments, the number of EG units is determined using matrix-assisted laser desorption/ionization-time of flight (MALDI-TOF) mass spectrometry.

C. Immunomodulatory Compounds

As described herein, the present disclosure relates to a synthetic nanoparticle comprising a PNA-amphiphile conjugate and an immunomodulatory compound, such as a cyclic dinucleotide (CDN).

Prokaryotic as well as eukaryotic cells use various small molecules for cell signaling and intra- and intercellular communication. Cyclic nucleotides like cGMP, cAMP, etc. are known to have regulatory and initiating activity in pro- and eukaryotic cells. Unlike eukaryotic cells, prokaryotic cells also use cyclic dinucleotides as regulatory molecules. In prokaryotes, the condensation of two OTP molecules is catalyzed by the enzyme diguanylate cyclase (DGC) to give cyclic diGMP (cdGMP), which represents an important regulator in bacteria. Recent work suggests that CDNs such as cdGMP or analogs thereof can also stimulate or enhance immune or inflammatory response in a patient or can enhance the immune response to a vaccine by serving as an adjuvant in mammals.

In certain embodiments, a CDN induces an innate immune response. In certain embodiments, an innate immune response effectively treats or prevents infections. In certain embodiments, a CDN induces a humoral and cellular immune response. In certain embodiments, a humoral and cellular immune response effectively treats or prevents cancer.

Cytosolic detection of pathogen-derived DNA requires signaling through TANK binding kinase 1 (TBK1) and its downstream transcription factor, IFN-regulatory factor 3 (IRF3). A transmembrane protein called STING (STimulator of Interferon Genes; also known as MITA, ERIS, MPYS and TMEM173) functions as the signaling receptor for these cyclic dinucleotides, causing stimulation of the TBK1-IRF3 signaling axis and a STING-dependent type I interferon response. Burdette et al., Nature 478: 515-18, 2011 demonstrated that STING binds directly to cyclic diguanylate monophosphate, but not to other unrelated nucleotides or nucleic acids.

Suitable cyclic dinucleotides for use in the present disclosure are described in some detail in, e.g., U.S. Pat. Nos. 7,709,458 and 7,592,326; WO 2007/054279; US 2014/0205653; and Yan et al. Bioorg. Med. Chem Lett. 18: 5631 (2008), each of which is hereby incorporated by reference.

In certain embodiments, cyclic dinucleotides include, but are not limited to, cdAMP, cdGMP, cdIMP, c-AMP-GMP, c-AMP-IMP, and c-GMP-IMP, and analogs thereof including, but not limited to, phosphorothioate analogues.

In certain embodiments, a cyclic dinucleotide is an agonist of STING (STimulator of Interferon Genes). As described above, the STING signaling pathway in immune cells is a central mediator of innate immune response and when stimulated, induces expression of various interferons, cytokines and T cell recruitment factors that amplify and strengthen immune activity. Recent work has shown that STING agonists are effective adjuvants and efficiently elicit an immune response, described, for example in Dubensky, T., et al., *Therapeutic Advances in Vaccines*, Vol. 1(4): 131-143 (2013); and Hanson, M., et al., *The Journal of Clinical Investigation*, Vol. 125 (6): 2532-2546 (2015), hereby incorporated by reference. However, delivery of STING agonists is problematic. The present disclosure is based in part on the discovery that a STING agonist can noncovalently complex with a peptide nucleic acid (PNA) oligomer, allowing for delivery.

In certain embodiments, a STING agonist is chemically synthesized. In certain embodiments, a STING agonist is an analog of a naturally occurring cyclic dinucleotide. STING agonists, including analogs of cyclic dinucleotides, suitable for use in the disclosure are provided in U.S. Pat. Nos. 7,709,458 and 7,592,326; and US 2014/0205653.

D. PNA-Amphiphile Conjugates and Nanoparticles

An amphiphile as described herein comprises a peptide nucleic acid (PNA) oligomer conjugated to a lipid. In certain embodiments, an amphiphile further comprises a polymer (e.g., polyethylene glycol). In certain embodiments, a PNA oligomer is conjugated to a first lipid and a polymer (e.g., polyethylene glycol) is conjugated to a second lipid. In certain embodiments, the first and second lipids are the same type of lipid. In certain embodiments, the first and second lipids are different types of lipids. In certain embodiments, the first and second lipid conjugates are combined to form an initial micellar structure.

In certain embodiments, a PNA oligomer and a polymer (e.g., polyethylene glycol) are conjugated to the same lipid. In certain embodiments, a PNA oligomer is conjugated to a lipid and a polymer (e.g., polyethylene glycol) is conjugated to the PNA oligomer. In certain embodiments, a polymer (e.g., polyethylene glycol) is conjugated to a lipid and a PNA oligomer is conjugated to the polymer (e.g., polyethylene glycol).

In certain embodiments, a population of PNA-amphiphile conjugates is non-covalently coupled to an immunomodulatory compound, such as a CDN, to form a nanoparticle. In general, the configuration of the PNA-amphiphile influences the resulting structure of the nanoparticle. For example, the number of guanine nucleosides present in a PNA oligomer may influence the confirmation of the resulting nanoparticle. In certain embodiments, the structure of the nanoparticle is selected from the group: worm-like micelle, disc-like micelle, nanofiber and spherical micelle. In certain embodiments, the structure of the nanoparticle is a worm-like micelle. In certain embodiments, the structure of the nanoparticle is a disc-like micelle. In certain embodiments, the structure of the nanoparticle is a nanofiber. In certain embodiments, the structure of the nanoparticle is a spherical micelle. In certain embodiments, the nanoparticle has a diameter ranging from 10 nm to 100 nm. In certain embodiments, the nanoparticle has a diameter ranging from 50 nm to 100 nm.

E. Linker

In certain embodiments, the PNA-amphiphile conjugate is formed by covalently coupling one or more hydrophobic lipids and a PNA oligomer and, optionally, one or more polymers. The covalent bond may be a non-cleavable linkage or a cleavable linkage. The non-cleavable linkage can include an amide bond or phosphate bond, and the cleavable linkage can include a disulfide bond, acid-cleavable linkage, ester bond, anhydride bond, biodegradable bond, or enzyme-cleavable linkage.

(i) Ethylene Glycol Linkers

In certain embodiments, the linker is one or more ethylene glycol (EG) units, or two or more EG units (i.e., polyethylene glycol (PEG)). For example, in certain embodiments, a peptide nucleic acid (PNA) oligomer and a hydrophobic lipid are chemically linked by a polyethylene glycol (PEG) molecule or a derivative or analog thereof.

In certain embodiments, amphiphiles suitable for use in the methods disclosed herein contain PNA oligomer linked to PEG which is in turn linked to a hydrophobic lipid, either covalently or via formation of amphiphiles that hybridize to micelles. The precise number of EG units depends on the lipid and the PNA oligomer, however, typically, a linker can have between about 1 and about 100, between about 20 and about 80, between about 30 and about 70, or between about 40 and about 60 EG units. In certain embodiments, the linker has between about 45 and 55 EG, units. For example, in certain embodiments, the linker has about 48 EG units or about 42 EG units.

(ii) Oligonucleotide Linkers

In certain embodiments, the linker is an oligonucleotide. The linker can have any sequence, for example, the sequence of the oligonucleotide can be a random sequence, or a sequence specifically chosen for its molecular or biochemical properties (e.g., highly polar). In certain embodiments, the linker includes one or more series of consecutive adenine (A), cytosine (C), guanine (G), thymine (T), uracil (U), or analog thereof In certain embodiments, the polar block linker consists of a series of consecutive adenine (A), cytosine (C), guanine (G), thymine (T), uracil (U), or analog thereof.

In certain embodiments, the linker is one or more guanines, for example between 1-10 guanines. In certain embodiments, altering the number of guanines between a PNA oligomer and/or a polymer and a lipid tail controls micelle stability in the presence of serum proteins. Therefore, the number of guanines in the linker can be selected based on the desired affinity of the conjugate for serum proteins such as albumin.

F. Immunogenic Compositions

The synthetic nanoparticles disclosed herein can be used in immunogenic compositions or as components in vaccines. Typically, immunogenic compositions disclosed herein include a PNA-amphiphile conjugate and an immunomodulatory compound (e.g., a CDN), an antigen, or a combination thereof. In some embodiments, a vaccine is formed by a combination of a PNA-amphiphile conjugate and an immunomodulatory compound with an antigen. When administered to a subject in combination, the PNA-amphiphile, immunomodulatory compound and antigen can be administered in separate pharmaceutical compositions, or they can be administered together in the same pharmaceutical composition. When administered in combination, the PNA-amphiphile and immunomodulatory compound can be a lipid conjugate, the antigen can be a lipid conjugate, or the PNA-amphiphile and immunomodulatory compound and the antigen can both be lipid conjugates.

An immunogenic composition can include a synthetic nanoparticle, administered alone, or in combination with an antigen. Antigens can be peptides, proteins, polysaccharides, saccharides, lipids, nucleic acids, or combinations thereof. The antigen can be derived from a virus, bacterium, parasite, plant, protozoan, fungus, tissue or transformed cell such as a cancer or leukemic cell and can be a whole cell or immunogenic component thereof, e.g., cell wall components or molecular components thereof.

Suitable antigens are known in the art and are available from commercial government and scientific sources. In one embodiment, the antigens are whole inactivated or attenuated organisms. These organisms may be infectious organisms, such as viruses, parasites and bacteria. These organisms may also be tumor cells. The antigens may be purified or partially purified polypeptides derived from tumors or viral or bacterial sources. The antigens can be recombinant polypeptides produced by expressing DNA encoding the polypeptide antigen in a heterologous expression system. The antigens can be DNA encoding all or part of an antigenic protein. The DNA may be in the form of vector DNA such as plasmid DNA.

Antigens may be provided as single antigens or may be provided in combination. Antigens may also be provided as complex mixtures of polypeptides or nucleic acids. Exemplary antigens are provided below.

(i) Peptide Antigens

In certain embodiments, the nanoparticle suitable for use in the methods disclosed herein includes an antigenic protein or polypeptide, such as a tumor-associated antigen or portion thereof, either conjugated to the amphiphile or administered separately.

In some embodiments, the peptide is 2-100 amino acids, including for example, 5 amino acids, 10 amino acids, 15 amino acids, 20 amino acids, 25 amino acids, 30 amino acids, 35 amino acids, 40 amino acids, 45 amino acids, or 50 amino acids. In some embodiments, a peptide is greater than 50 amino acids. In some embodiments, the peptide is >100 amino acids.

In some embodiments, a protein/peptide is linear, branched or cyclic. The peptide can include D amino acids, L amino acids, or a combination thereof. In some embodiments, the peptide or protein is conjugated to the PNA oligomer, lipid, or polymer at the N-terminus or the C-terminus of the peptide or protein.

In some embodiments, the protein or polypeptide is any protein or peptide that can induce or increase the ability of the immune system to develop antibodies and T-cell responses to the protein or peptide.

Suitable antigens are known in the art and are available from commercial government and scientific sources. In certain embodiments, the antigens are whole inactivated or irradiated tumor cells. The antigens may be purified or partially purified polypeptides derived from tumors. In some embodiments, the antigens are recombinant polypeptides produced by expressing DNA encoding the polypeptide antigen in a heterologous expression system. In some embodiments, the antigens are DNA encoding all or part of an antigenic protein. The DNA may be in the form of vector DNA such as plasmid DNA.

In certain embodiments, antigens are provided as single antigens or are provided in combination. In some embodiments, antigens are provided as complex mixtures of polypeptides or nucleic acids.

(ii) Viral Antigens

In some embodiments, the nanoparticle suitable for use in the methods disclosed herein includes a viral antigen. In some embodiments, the viral antigen is isolated from any virus including, but not limited to, a virus from any of the following viral families: Arenaviridae, Arterivirus, Astroviridae, Baculoviridae, Badnavirus, Bamaviridae, Birnaviridae, Bromoviridae, Bunyaviridae, Caliciviridae, Capillovirus, Carlavirus, Caulimovirus, Circoviridae, Closterovirus, Comoviridae, Coronaviridae (e.g., Coronavirus, such as severe acute respiratory syndrome (SARS) virus), Corticoviridae, Cystoviridae, Deltavirus, Dianthovirus, Enamovirus, Filoviridae (e.g., Marburg virus and Ebola virus (e.g., Zaire, Reston, Ivory Coast, or Sudan strain)), Flaviviridae, (e.g., Hepatitis C virus, Dengue virus 1, Dengue virus 2, Dengue virus 3, and Dengue virus 4), Hepadnaviridae, Herpesviridae (e.g., Human herpesvirus 1, 3, 4, 5, and 6, and Cytomegalovirus), Hypoviridae, Iridoviridae, Leviviridae, Lipothrixviridae, Microviridae, Orthomyxoviridae (e.g., Influenzavirus A and B and C), Papovaviridae, Paramyxoviridae (e.g., measles, mumps, and human respiratory syncytial virus), Parvoviridae, Picornaviridae (e.g., poliovirus, rhinovirus, hepatovirus, and aphthovirus), Poxyiridae (e.g., vaccinia and smallpox virus), Reoviridae (e.g., rotavirus), Retroviridae (e.g., lentivirus, such as human immunodeficiency virus (HIV) 1 and HIV 2), Rhabdoviridae (for example, rabies virus, measles virus, respiratory syncytial virus, etc.), Togaviridae (for example, rubella virus, dengue virus, etc.), and Totiviridae. Suitable viral antigens also include all or part of Dengue protein M, Dengue protein E, Dengue D1NS1, Dengue D1NS2, and Dengue D1NS3.

In some embodiments, viral antigens are derived from a particular strain such as a papilloma virus, a herpes virus, e.g., herpes simplex 1 and 2; a hepatitis virus, for example, hepatitis A virus (HAV), hepatitis B virus (HBV), hepatitis C virus (HCV), the delta hepatitis D virus (HDV), hepatitis E virus (HEV) and hepatitis G virus (HGV), the tick-borne encephalitis viruses; parainfluenza, varicella-zoster, cytomeglavirus, Epstein-Barr, rotavirus, rhinovirus, adenovirus, coxsackieviruses, equine encephalitis, Japanese encephalitis, yellow fever, Rift Valley fever, and lymphocytic choriomeningitis.

(iii) Bacterial Antigens

In some embodiments, the nanoparticle suitable for use in the methods disclosed herein includes a bacterial antigen. In some embodiments, the bacterial antigen originates from any bacteria including, but not limited to, *Actinomyces, Anabaena, Bacillus, Bacteroides, Bdellovibrio, Bordetella,*

*Borrelia, Campylobacter, Caulobacter, Chlamydia, Chlorobium, Chromatium, Clostridium, Corynebacterium, Cytophaga, Deinococcus, Escherichia, Francisella, Halobacterium, Heliobacter, Haemophilus, Hemophilus* influenza type B (HIB), *Hyphomicrobium, Legionella, Leptspirosis, Listeria, Meningococcus* A, B and C, *Methanobacterium, Micrococcus, Myobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus, and Treponema, Vibrio*, and *Yersinia*.

(iv) Parasite Antigens

In some embodiments, the nanoparticle suitable for use in the methods disclosed herein includes a parasite antigen. In some embodiments, parasite antigens are obtained from parasites such as, but not limited to, *Cryptococcus neolormans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Topanosoma brucei, Entamoeba histolytica, Toxoplasma gondii, Trichomonas vaginalis* and *Schistosoma mansoni*. These include Sporozoan antigens, Plasmodian antigens, such as all or part of a Circumsporozoite protein, a Sporozoite surface protein, a liver stage antigen, an apical membrane associated protein, or a Merozoite surface protein.

(v) Allergens and Environmental Antigens

In some embodiments, the nanoparticle suitable for use in the methods disclosed herein includes an allergen or environmental antigen. In some embodiments, the allergen or environmental antigen, is an antigen derived from naturally occurring allergens such as pollen allergens (tree-, herb, weed-, and grass pollen allergens), insect allergens (inhalant, saliva and venom allergens), animal hair and dandruff allergens, and food allergens. Important pollen allergens from trees, grasses and herbs originate from the taxonomic orders of Fagales, Oleales, Pinales and platanaceae including i.a. birch (*Betula*), alder (*Alnus*), hazel (*Corylus*), hornbeam (*Carpinus*) and olive (*Olea*), cedar (*Cryptomeria* and *Juniperus*), Plane tree (*Platanus*), the order of Poales including e.g., grasses of the genera *Lolium, Phleum, Poa, Cynodon, Dactylis, Holcus, Phalaris, Secale*, and *Sorghum*, the orders of Asterales and Urticales including i.a. herbs of the genera *Ambrosia, Artemisia*, and *Parietaria*. Other allergen antigens that may be used include allergens from house dust mites of the genus *Dermatophagoides* and *Euroglyphus*, storage mite e.g *Lepidoglyphys, Glycyphagus* and *Tyrophagus*, those from cockroaches, midges and fleas e.g. *Blatella, Periplaneta, Chironomus* and *Clenocepphalides*, those from mammals such as cat, dog and horse, birds, venom allergens including such originating from stinging or biting insects such as those from the taxonomic order of Hymenoptera including bees (superfamily Apidae), wasps (superfamily Vespidea), and ants (superfamily Formicoidae). Still other allergen antigens that may be used include inhalation allergens from fungi such as from the genera *Alternaria* and *Cladasporium*.

(iv) Cancer Antigens

In some embodiments, the nanoparticle suitable for use in the methods disclosed herein includes a cancer antigen A cancer antigen is an antigen that is typically expressed preferentially by cancer cells (i.e., it is expressed at higher levels in cancer cells than on non-cancer cells) and in some instances it is expressed solely by cancer cells. In some embodiments, the cancer antigen is expressed within a cancer cell or on the surface of the cancer cell. In some embodiments, the cancer antigen is MART-1/Melan-A, gp100, adenosine deaminase-binding protein (ADAbp), FAP, cyclophilin b, colorectal associated antigen (CRC)—C017-1A/GA733, carcinoembryonic antigen (CEA), CAP-1, CAP-2, etv6, AML1, prostate specific antigen (PSA), PSA-1, PSA-2, PSA-3, prostate-specific membrane antigen (PSMA), T cell receptor/CD3-zeta chain, and CD20. The cancer antigen may be selected from the group consisting of MAGE-A1, MAGE-A2, MAGE-A3, MAGE-A4, MAGE-A5, MAGE-A6, MAGE-A7, MAGE-A8, MAGE-A9, MAGE-A10, MAGE-A11, AGE-A12, MAGE-Xp2 (MAGE B2), MAGE-Xp3 (MAGE-B3), MAGE-Xp4 (MAGE-B4), MAGE-C1, MAGE-C2, MAGE-C3, MAGE-C4, MAGE-05), GAGE-1, GAGE-2, GAGE-3, GAGE-4, GAGE-5, GAGE-6, GAGE-7, GAGE-8, GAGE-9, BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin, γ-catenin, p120ctn, gp100Pmel117, PRAME, NY-ESO-1, cdc27, adenomatous polyposis coli protein (APC), fodrin, Connexin 37, Ig-idiotype, p15, gp75, GM2 ganglioside, GD2 ganglioside, human papilloma virus proteins, Smad family of tumor antigens, Imp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, CD20, or c-erbB-2.

G. Micelle-Stabilizing Conjugates

Micelle-stabilizing conjugates include synthetic nanoparticles that accumulate in the tissue surrounding the site of delivery. The conjugates typically do not bind to albumin. In some embodiments, the lipid used to prepare a micelle-stabilizing conjugate is the same as the lipid used in the amphiphiles discussed above, and the ability to resist binding to albumin is controlled by the molecular or biochemical properties of the PNA, the linker, or a combination thereof. In some embodiments, lipids that would not be effective for use in lymph node targeted conjugates are useful in micelle-stabilizing conjugates because the micelle-stabilizing conjugates do not necessarily have to bind to albumin.

Micelle-stabilizing conjugates can be selected based on the ability to spontaneously form micelles in aqueous solution that are not disrupted by serum components such as albumin, as discussed above. Suitable methods for testing the ability of the lipid, amphiphile, or nanoparticle to bind to albumin are known in the art. For example, in one embodiment, a plurality of amphiphiles is allowed to spontaneously form micelles in aqueous solution. The micelles are incubated with albumin, or a solution including albumin such Fetal Bovine Serum (FBS). Samples can be analyzed, for example, by ELISA, diameter separation chromatography or other methods to determine if binding has occurred. Amphiphiles or synthetic nanoparticles can be selected as micelle stabilized conjugates if in the presence of albumin, or a solution including albumin such Fetal Bovine Serum (FBS), the micelles remain intact and the lipid conjugates do not bind to albumin.

In certain embodiments, lipids for use in micelle-stabilizing lipid conjugates include, but are not limited to fatty acids with aliphatic tails of 8-30 carbons including, but not limited to, linear and unsaturated and saturated fatty acids, branched saturated and unsaturated fatty acids, and fatty acids derivatives, such as fatty acid esters, fatty acid amides, and fatty acid thioesters, diacyl lipids, Cholesterol, Cholesterol derivatives, and steroid acids such as bile acids; Lipid A or combinations thereof.

In sonic embodiments, the lipid is a diacyl lipid or two-tailed lipid. In some embodiments, the tails in the diacyl lipid contain from about 8 to about 30 carbons and can be saturated, unsaturated, or combinations thereof. The tails can be coupled to the head group via ester bond linkages, amide bond linkages, thioester bond linkages, or combinations thereof. In a particular embodiment, the diacyl lipids are phosphate lipids, glycolipids, sphingolipids, or combinations thereof.

Micelle-stabilizing, conjugates can form micelles spontaneously in aqueous solution by self-assembly. The micelle has a hydrophobic lipid core and a hydrophilic surface. Formation of a micelle in an aqueous environment (e.g., water, buffer) is driven by hydrophobic interactions.

In some embodiments, micelles of a homogeneous micelle population are substantially uniform in diameter.

The diameter of a micelle as described herein can be from about 3 nm to about 100 nm. In some embodiments, the diameter of a micelle is 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 20 nm, 21 nm, 22 nm, 23 nm, 24 nm, 25 nm, 26 nm, 27 nm, 28 nm, 29 nm, 30 nm, 31 nm, 32 nm, 33 nm, 34 nm, 35 nm, 36 nm, 37 nm, 38 nm, 39 nm, 40 nm, 41 nm, 42 nm, 43 nm, 44 nm, 45 nm, 46 nm, 47 nm, 48 nm, 49 nm, 50 nm, 51 nm, 52 nm, 53 nm, 54 nm, 55 nm, 56 nm, 57 nm, 58 nm, 59 nm, 60 nm, 61 nm, 62 nm, 63 nm, 64 nm, 65 nm, 66 nm, 67 nm, 68 nm, 69 nm, 70 nm, 71 nm, 72 nm, 73 nm, 74 nm, 75 nm, 76 nm, 77 nm, 78 nm, 79 nm, 80 nm, 81 nm, 82 nm, 83 nm, 84 nm, 85 nm, 86 nm, 87 nm, 88 nm, 89 nm, 90 nm, 91 nm, 92 nm, 93 am, 94 nm, 95 nm, 96 nm, 97 nm, 98 nm, 99 nm, or 100 nm. In some embodiments, the diameter of a micelle is about 20 nm or about 50 nm.

Methods of Making PNA-Amphiphile Conjugates and Nanoparticles

A. PNA-Amphiphile Conjugates

In certain embodiments, a synthetic nanoparticle comprises a PNA-amphiphile noncovalently complexed with an immunomodulatory compound. A PNA-amphiphile suitable for use in a nanoparticle described herein comprises a hydrophilic peptide nucleic acid (PNA) oligomer conjugated to a hydrophobic lipid. Methods of making PNA oligomers are known in the art, and described, for example in U.S. Pat. Nos. 5,539,082 and 7,223,833; and WO 92/20702. Lipids suitable for use in the synthetic nanoparticles are described herein, and for example, in US 2013/0295129, herein incorporated by reference. To generate the amphiphile, a PNA oligomer is conjugated to a lipid. Methods of conjugating PNA oligomers to other moieties, including lipids and polymers are known in the art, and described for example in U.S. Pat. Nos. 5,539,082 and 7,223,833. In certain embodiments, a lipid tail is conjugated to a PNA oligomer described herein through formation of an amide bond with the N-terminus amine at the final step of solid-phase synthesis before cleavage from the resin. In certain embodiments, a lipid tail is conjugated to a PNA oligomer described herein through a carbamate of a urea bond using a similar method. In certain embodiments, a lipid tail is conjugated to a PNA oligomer described herein with a cysteine through a reaction with maleimide-containing lipid or lipid-polymer, such as DSPE-PEG-maleimide.

In certain embodiments, the PNA-amphiphile has the following Structure I:

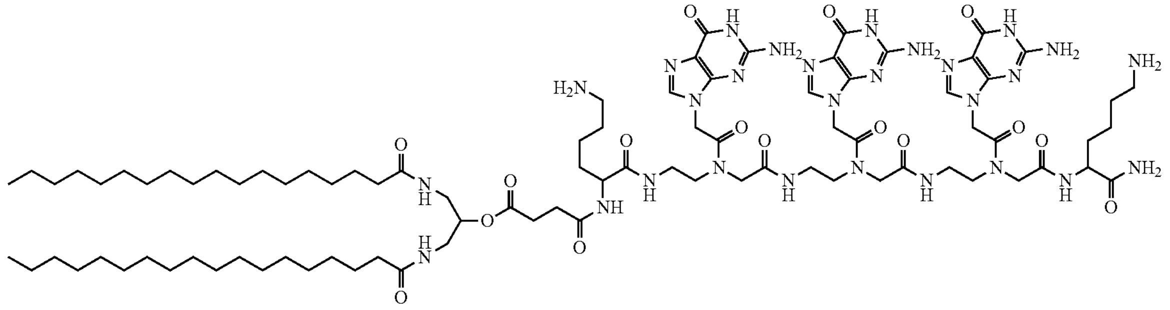

MALDi-tof: $MH^+$ Expected 1852, Found 1852

In certain embodiments, a PNA-amphiphile for use in a synthetic nanoparticle described herein further comprises a polymer. In certain embodiments, a polymer is conjugated to a lipid directly. In certain embodiments, a polymer is conjugated to a lipid via a linker. In certain embodiments, a polymer is conjugated to a PNA oligomer, which is conjugated to a lipid. In certain embodiments, a cysteine residue is added to the C-terminus of a PNA oligomer, to introduce a free thiol for further conjugation reactions. A PNA oligomer comprising a free thiol can be reacted with a polymer to conjugate the polymer to the PNA oligomer. In certain embodiments, a polymer is polyethylene glycol.

In certain embodiments, a PNA-amphiphile with a C-terminal cysteine has the following Structure II:

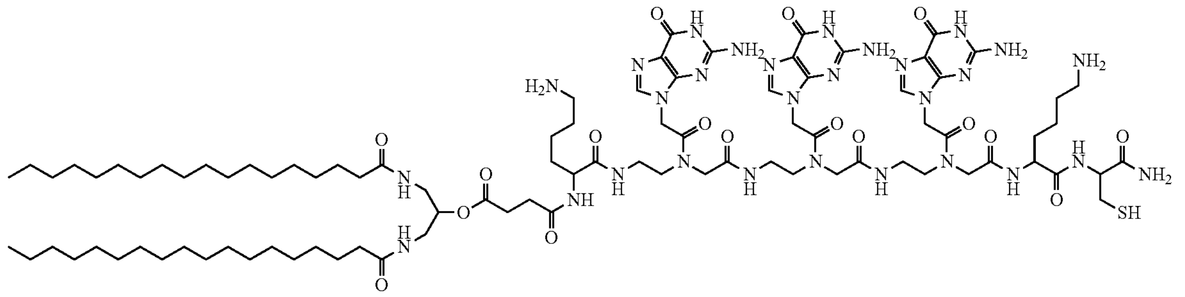
MALDI-tof: $MH^+$ Expected
1955. Found 1955
In certain embodiments, a PNA-amphiphile conjugated to a polymer (i.e., methoxy-poly(ethylene glycol)-maleimide) has the following Structure III in which an average of 42 units of PEG are covalently coupled to the C-terminus of a PNA oligomer:
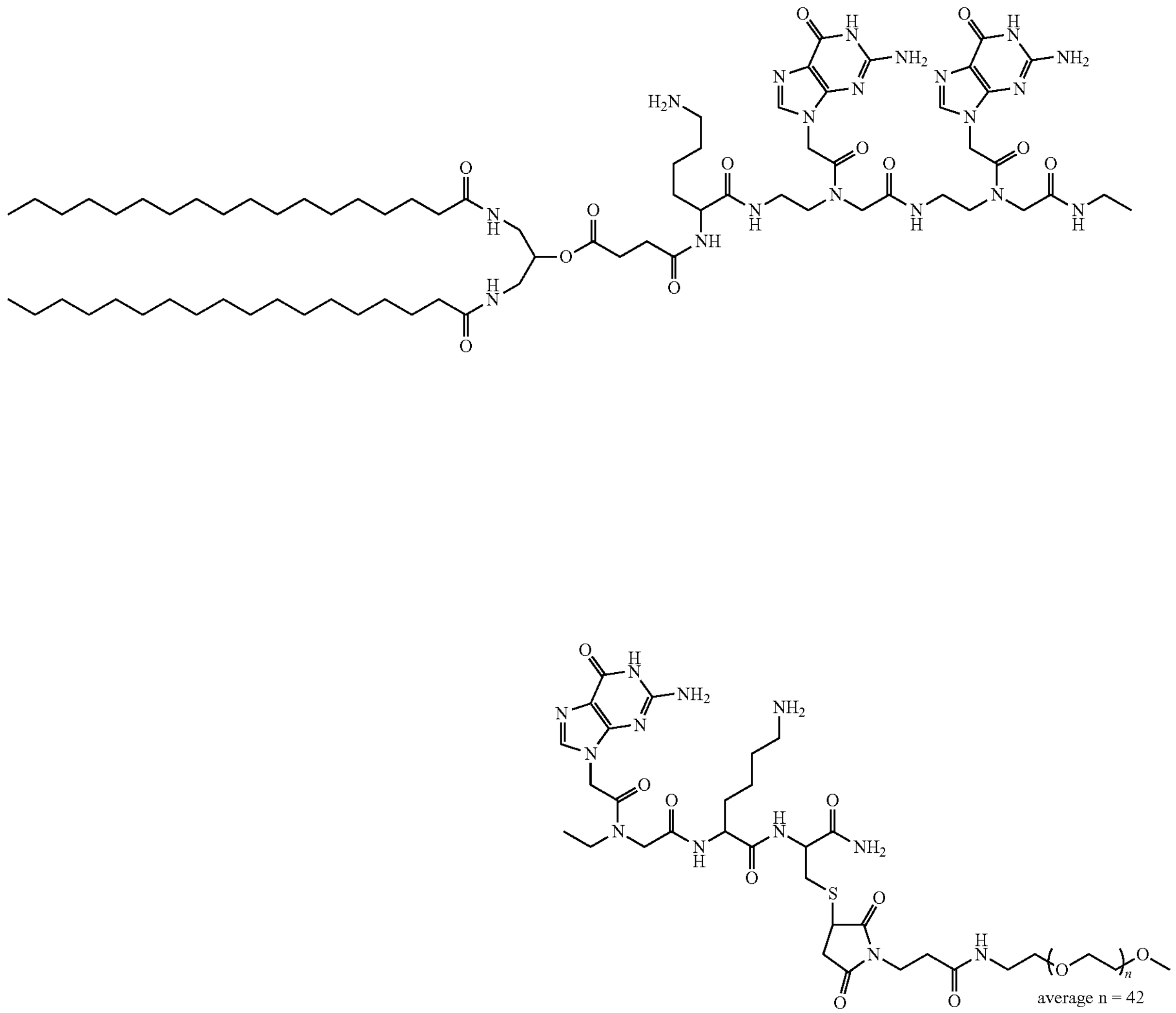
MALDI-tof: $MH^+$ Expected
4031, Found 4030

In some embodiments, a PNA-amphiphile has a structure selected from the following group:
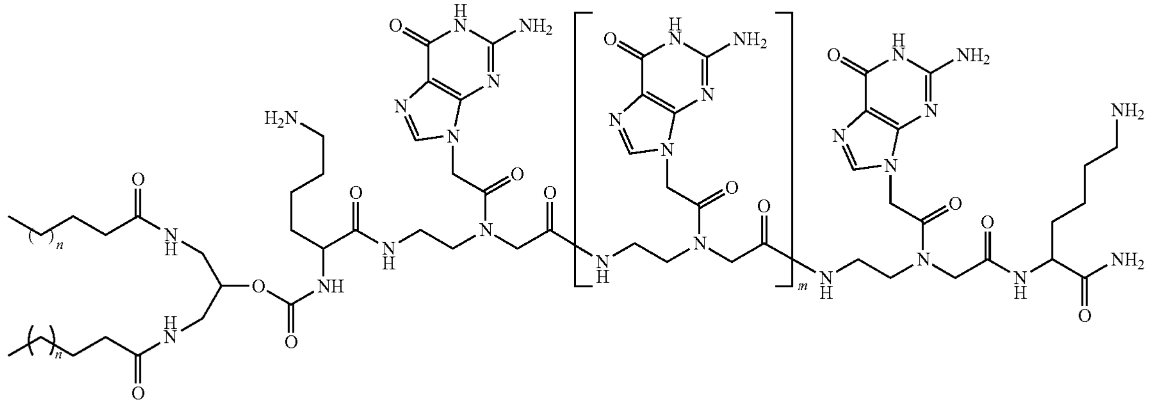
1 n = 12, m = 1
2 n = 14, m = 1
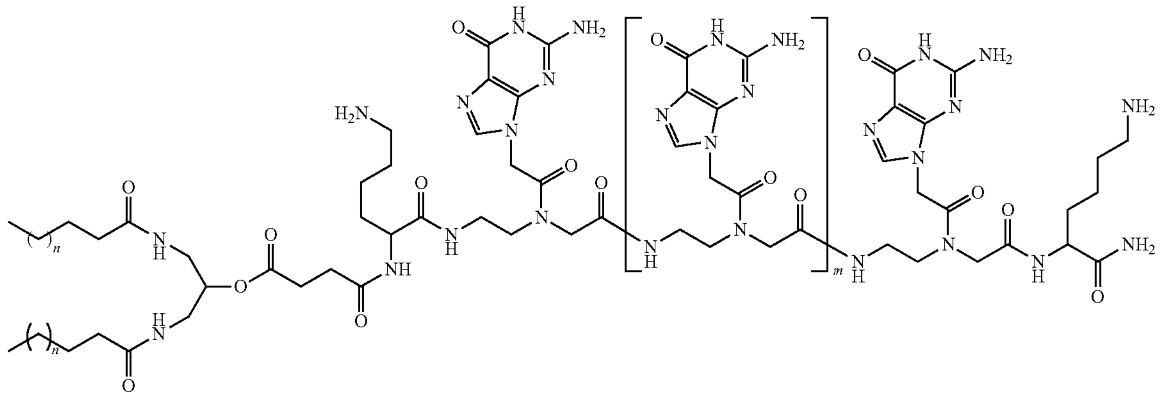
3 n = 12, m = 1
4 n = 14, m = 1
5 n = 12, m = 3
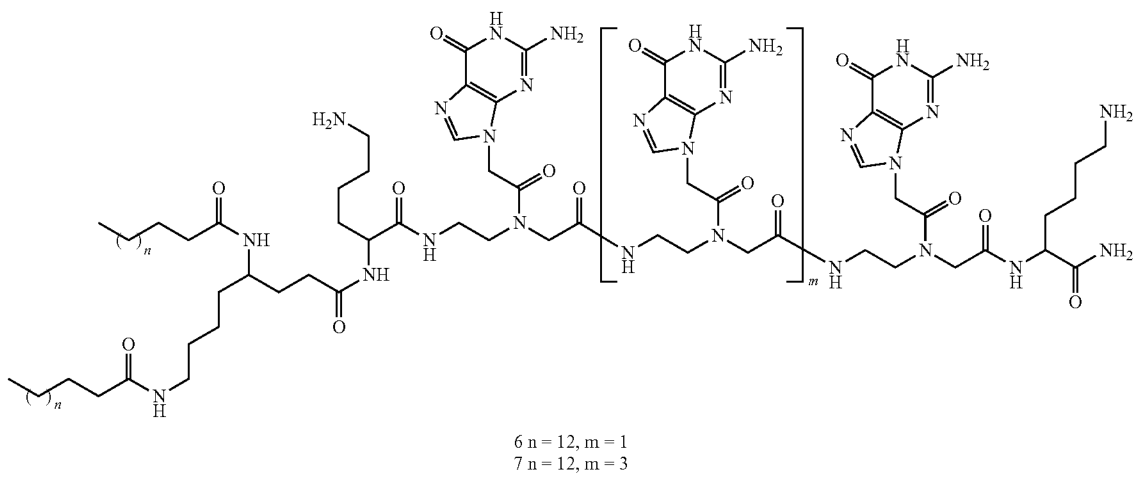
6 n = 12, m = 1
7 n = 12, m = 3

-continued
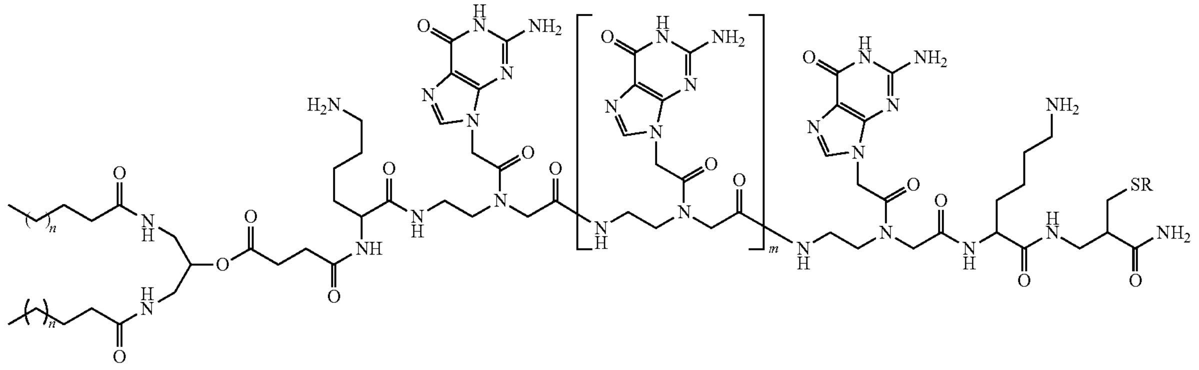
8 n = 14, m = 1, R = H
9 n = 14, m = 1, R = PEG2K-maleimide
In some embodiments, a PNA-amphiphile has the following structure:
1
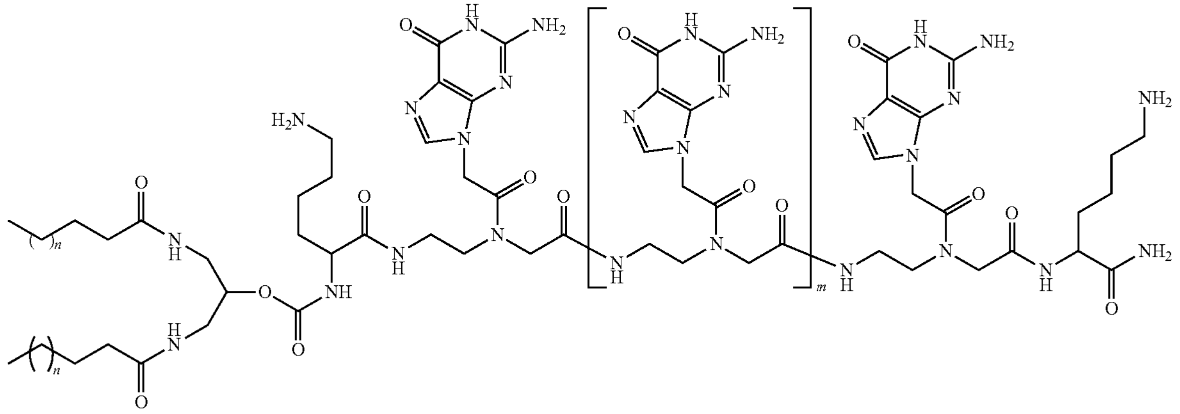
n = 12, m =1
In some embodiments, a PNA-amphiphile has the following structure:
2
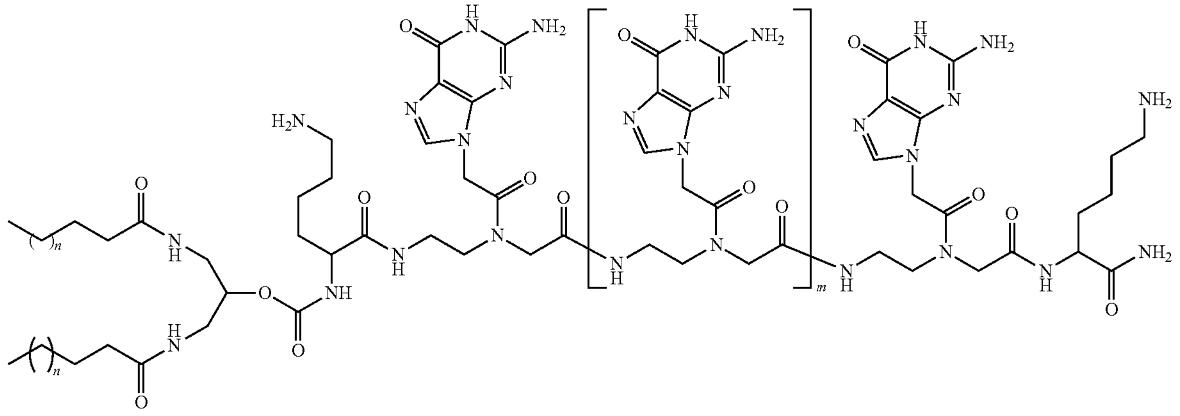
n = 14, m =1

In some embodiments, a PNA-amphiphile has the following structure:

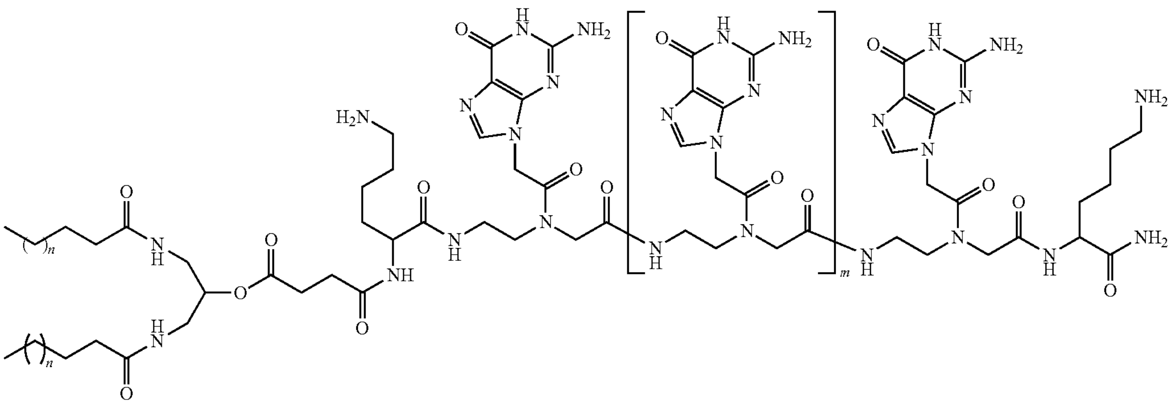

n = 12, m =3

B. Synthetic Nanoparticles

Figure 1B:
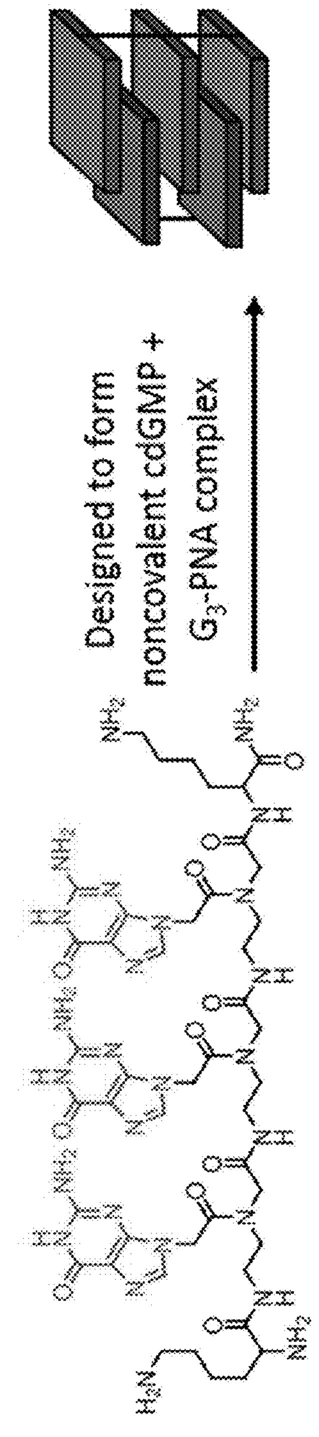
FIG. 1B depicts the chemical structure of a peptide nucleic acid (PNA) oligomer containing three guanine bases ($G_3$-PNA) and two lysines designed to form a noncovalent complex with cdGMP and a schematic of the complex.

In certain embodiments, a PNA-amphiphile is combined with an immunomodulatory compound, i.e., cyclic dinucleotide (CDN), to generate a synthetic nanoparticle. In some embodiments, a CDN forms a specific noncovalent complex with a PNA oligomer, as shown in FIG. 1B. Methods for synthesizing a CDN are known in the art, and are described herein and in U.S. Pat. Nos. 7,709,458 and 7,592,326; WO 2007/0541279; US 2014/0205653; and Yan et al. Bioorg. Med. Chem Lett. 18: 5631 (2008), Dubensky, T., et al., *Therapeutic Advances in Vaccines*, Vol. 1(4): 131-143 (2013); and Hanson, M., et al., *The Journal of Clinical Investigation*, Vol. 125 (6): 2532-2546 (2015).

In some embodiments, a CDN is added to a solution comprising a PNA-amphiphile conjugate to form a nanoparticle. In some embodiments, a complex of CDN and PNA oligomer is driven by hydrophobic interactions through nucleic acid base stacking (e.g., pi-pi stacking). This interaction is specific to cyclic dinucleotides. In certain embodiments, the complex is not highly cationic and therefore does not cause significant toxicity. In certain embodiments, the noncovalent complex is formed through nucleic acid base staking interactions and hydrogen-bonding.

Confirmation that a noncovalent complex has been formed between the PNA oligomer of a PNA-amphiphile conjugate and a CDN can be determined using methods routinely used in the art. In certain embodiments, formation of a noncovalent complex between a PNA oligomer and a CDN is confirmed by measuring UV absorbance at 260 nm. Base stacking results in a hypochromic shift that is lost upon dissociation of the complex. The formation of hydrogen bonds can be monitored by $^1$H-NMR spectroscopy based on shifts in specific proton resonances, hydrogen-deuterium exchange, and through nuclear Overhauser effect (NOE) 1D and 2D experiments. The labeling of the PNA amphiphile and the CDN with a FRET donor-acceptor pair allows complex formation to be monitored through fluorescence spectroscopy as a function of temperature, concentration, and additives, such as serum proteins. The association constant and thermodynamics of binding can be determined using isothermal titration calorimetry.

In some embodiments, a PNA-amphiphile conjugate and an immunomodulatory compound self-assemble to form a nanoparticle. In certain embodiments, nanoparticle formation occurs upon addition of CDN to a population of PNA-amphiphile conjugates. In certain embodiments, a nanoparticle has a structure selected from the following group: worm-like micelle, disc-like micelle, nanofiber and spherical micelle. In certain embodiments, the structure of a nanoparticle is influenced by the structure of the PNA oligomer and by the configuration of the amphiphile (i.e., where a polymer is conjugated to an amphiphile). For example, a higher number of nucleobases in a PNA oligomer (e.g., 6, 7, 8, 9 or 10 guanine nucleosides or more), may result in formation of a nanoparticle having a nanofiber structure. In contrast, a lower number of nucleobases in a PNA oligomer may result in formation of a nanoparticle having a spherical micelle structure. In certain embodiments, conjugation of a polymer to a PNA oligomer conjugated to a lipid may influence the nanoparticle structure compared to the structure resulting from conjugation of a PNA oligomer to a polymer conjugated to a lipid.

The structure of a nanoparticle is determined using methods routinely used in the art. For example, the structure of a nanoparticle can be observed using cryo-electron microscopy (cryo-EM or cryo-TEM), which take pictures of a sample containing a population of self-assembled nanoparticles. In certain embodiments, dynamic light scattering (DLS) or laser diffraction is used to determine the structure of a nanoparticle. Small-angle and wide-angle X-ray scattering is used to characterization nanoscale periodicities, for example bilayer d-spacings, and nanoparticle structure.

In certain embodiments, the structure of the synthetic nanoparticle may influence the use or application of the nanoparticle to subjects. For example, a nanoparticle having a nanofiber structure may disperse in a tumor but may not disperse systematically, thus being useful for intratumoral administration. In another example, a nanoparticle having a worm-like micelle structure may be delivered to the lymph nodes and therefore would be useful in stimulating an immune response.

Uses of Synthetic Nanoparticles and PNA-Amphiphile Conjugates

A. Cancer and Cancer Immunotherapy

A synthetic nanoparticle described herein is useful for treating a disorder associated with abnormal apoptosis or a differentiative process (e.g., cellular proliferative disorders (e.g., hyperproliferative disorders) or cellular differentiative disorders, such as cancer). Non-limiting examples of cancers that are amenable to treatment with the methods of the present disclosure are described below.

Examples of cellular proliferative and/or differentiative disorders include cancer (e.g., carcinoma, sarcoma, metastatic disorders or hematopoietic neoplastic disorders, e.g., leukemias). A metastatic tumor can arise from a multitude of primary tumor types, including but not limited to those of prostate, colon, lung, breast and liver. Accordingly, the compositions used herein, comprising, e.g., a synthetic nanoparticle, can be administered to a patient who has cancer.

As used herein, the terms "cancer" (or "cancerous"), "hyperproliferative," and "neoplastic" refer to cells having the capacity for autonomous growth (i.e., an abnormal state or condition characterized by rapidly proliferating cell growth). Hyperproliferative and neoplastic disease states may be categorized as pathologic (i.e., characterizing or constituting a disease state), or categorized as non-pathologic (i.e., as a deviation from normal but not associated with a disease state). The terms are meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasm" are used to refer to malignancies of the various organ systems, including those affecting the lung, breast, thyroid, lymph glands and lymphoid tissue, gastrointestinal organs, and the genitourinary tract, as well as to adenocarcinomas which are generally considered to include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the synthetic nanoparticle described herein is used to treat patients who have, who are suspected of having, or who may be at high risk for developing any type of cancer, including renal carcinoma or melanoma, or any viral disease. Exemplary carcinomas include those forming from tissue of the cervix, lung, prostate, breast, head and neck, colon and ovary. The term also includes carcinosarcomas, which include malignant tumors composed of carcinomatous and sarcomatous tissues. An "adenocarcinoma" refers to a carcinoma derived from glandular tissue or in which the tumor cells form recognizable glandular structures.

Additional examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias (e.g., erythroblastic leukemia and acute megakaryoblastic leukemia). Additional exemplary myeloid disorders include, but are not limited to, acute promyeloid leukemia (APML), acute myelogenous leukemia (AML) and chronic myelogenous leukemia (CIVIL) (reviewed in Vaickus, L. (1991) Crit. Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macro globulinemia (WM). Additional forms of malignant lymphomas include, but are not limited to non-Hodgkin lymphoma and variants thereof, peripheral T cell lymphomas, adult T cell leukemia/lymphoma (ATL), cutaneous T cell lymphoma (CTCL), large granular lymphocytic leukemia (LGF), Hodgkin's disease and Reed-Sternberg disease.

It will be appreciated by those skilled in the art that amounts of a synthetic nanoparticle that are sufficient to reduce tumor growth and diameter, or a therapeutically effective amount, will vary not only on the particular compounds or compositions selected, but also with the route of administration, the nature of the condition being treated, and the age and condition of the patient, and will ultimately be at the discretion of the patient's physician or pharmacist. The length of time during which the compounds used in the instant method will be given varies on an individual basis.

In certain embodiments, the synthetic nanoparticle disclosed herein is used to treat cancer. In certain embodiments, the synthetic nanoparticle disclosed herein is used in combination with an antigen to treat cancer. In certain embodiments, the synthetic nanoparticle disclosed herein is used to treat melanoma, leukemia, lung cancer, breast cancer, prostate cancer, ovarian cancer, colon cancer, and brain cancer.

In certain embodiments, the synthetic nanoparticle disclosed herein inhibits the growth and/or proliferation of tumor cells.

In certain embodiments, the synthetic nanoparticle disclosed herein reduces tumor diameter.

In certain embodiments, the synthetic nanoparticle disclosed herein inhibits metastases of a primary tumor.

It will be appreciated by those skilled in the art that reference herein to treatment extends to prophylaxis as well as the treatment of the noted cancers and symptoms.

In certain embodiments, the synthetic nanoparticle disclosed herein is used for cancer immunotherapy. The term "cancer immunotherapy" refers to treatment of a subject afflicted with, or at risk of suffering a recurrence of cancer, by a method comprising inducing, enhancing, suppressing, or otherwise modifying an immune response.

B. Infectious Diseases

In certain embodiments, a synthetic nanoparticle described herein is useful for treating acute or chronic infectious diseases. Because viral infections are cleared primarily by T-cells, an increase in T-cell activity is therapeutically useful in situations where more rapid or thorough clearance of an infective viral agent would be beneficial to an animal or human subject. Thus, in some embodiments the synthetic nanoparticles are administered for the treatment of local or systemic viral infections, including, but not limited to, immunodeficiency (e.g., HIV), papilloma (e.g., HPV), herpes (e,g., HSV), encephalitis, influenza (e.g., human influenza. virus A), and common cold (e.g., human rhinovirus) viral infections. In some embodiments, pharmaceutical formulations including the synthetic nanoparticles are administered topically to treat viral skin diseases such as herpes lesions or shingles, or genital warts. In some embodiments, the synthetic nanoparticles are administered to treat systemic viral diseases, including, but not limited to, AIDS, influenza, the common cold, or encephalitis.

Representative infections that can be treated, include but are not limited to infections cause by microorganisms including, but not limited to, *Actinomyces, Anabaena, Bacillus, Bacteroides, Bdellovibrio, Bordetella, Borrelia, Campy-*

*lobacter, Caulobacter, Chlamydia, Chlorobium, Chromatium, Clostridium, Corynebacterium, Cytophaga, Deinococcus, Escherichia, Francisella, Halobacterium, Heliobacter, Haemophilia, Hemophilus influenza* type B (HIB), *Histoplasma, Hyphomicrobium, Legioneila, Leishmania, Leptspirasis, Listeria, Meningococcus* and C, *Methanobacterium, Micrococcus, Myobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus*, and *Treponema, Vibrio, Yersinia, Crytococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Plasmodium vivax, Trypanosoma brucei, Entamoeba histolytica, Toxoplasma gondii, Trichomonas vaginalis* and *Schistosoma mansoni*.

In certain embodiments, the type of disease to be treated or prevented is a chronic infectious disease caused by a bacterium, virus, protozoan, helminth, or other microbial pathogen that enters intracellularly and is attacked, e.g., by cytotoxic T lymphocytes.

In certain embodiments, the type of disease to be treated or prevented is an infectious disease in the lungs caused by a bacterium. In certain embodiments, the synthetic nanoparticles inhibit biofilm formation of a bacterium. Inhibition of biofilm production by cyclic dinucleotides has been shown, for example, by Zogaj, X., et al., *Infection and Immunity*, Vol. 80(12): 4239-4247 (2012); and Yan, W., et al., *Microbiological Research*, Vol. 165: 87-96 (2010), each hereby incorporated by reference. Methods of measuring biofilm production are known in the art. For example, biofilm production can be measured by crystal violet staining and measurement of optical density of extracted crystal violet, or by the methods described in Ahn, S., et al., *Journal of Bacteriology*, Vol. 187 (9): 3028-3038 (2005), hereby incorporated by reference.

C. Increasing an Immune Response

In some embodiments, synthetic nanoparticles described herein are administered in an effective amount to induce, increase or enhance an immune response. The "immune response" refers to responses that induce, increase, or perpetuate the activation or efficiency of innate or adaptive immunity. Further, in some embodiments synthetic nanoparticles administered in the absence of other adjuvants are used to promote tolerance rather than immunity, to an allergen or autoimmune antigen. In some embodiments, the synthetic nanoparticles are delivered parenterally (by subcutaneous, intradermal, or intramuscular injection) through the lymphatics, or by systemic administration through the circulatory system. It is noted that the lymph nodes can filter albumin-bound conjugates. Therefore, in some embodiments parenteral administration does not result in systemic distribution as the nanoparticles may be preferentially filtered by the closest lymph node(s). This tendency also reduces systemic toxicity such as swelling of the spleen.

Accordingly, in some embodiments, the synthetic nanoparticles are administered at a site adjacent to or leading to one or more lymph nodes which are close to the site in need of an immune response (i.e., close to a tumor or site of infection). In some embodiments, the release profile of the immunomodulatory compound from the PNA-amphiphile is such that the synthetic nanoparticles are suitable for intradermal, subcutaneous or intramuscular injection, wherein the immunomodulatory compound is released in the lymphatics, where a desired immune response is achieved. In some embodiments, the immunomodulatory compound is released over about 6-24 hours. In some embodiments, the immunomodulatory compound is released over about 12-24 hours. In some embodiments, the immunomodulatory compound is released over about 24 hours. In some embodiments, the synthetic nanoparticles are administered in multiple doses at various locations throughout the body. In some embodiments, the synthetic nanoparticles are administered directly to a site in need of an immune response (e.g., a tumor or site of infection).

In some embodiments, the immune response is induced, increased, or enhanced by the synthetic nanoparticles compared to a control, for example an immune response in a subject induced, increased, or enhanced by the immunomodulatory compound alone, or the immunomodulatory compound delivered using an alternative delivery strategy such as liposomes. As discussed in more detail below, in some embodiments, synthetic nanoparticles reduce inactivation and/or prolong activation of T cells (i.e., increase antigen-specific proliferation of T cells, enhance cytokine production by T cells, stimulate differentiation ad effector functions of cells and/or promote T cell survival) or overcome cell exhaustion and/or anergy.

In some embodiments, the synthetic nanoparticles are used, for example, to induce an immune response, when administering the immunomodulatory compound alone, or the immunomodulatory compound in combination with an alternative delivery system, is ineffectual. In some embodiments, the synthetic nanoparticles are also used to enhance or improve the immune response compared to administering immunomodulatory compound alone. In some embodiments, the synthetic nanoparticles reduce the dosage required to induce, increase, or enhance an immune response; or reduce the time needed for the immune system to respond following administration.

In some embodiments, the synthetic nanoparticles are administered in an effective amount to induce or increase the activation of STING. In some embodiments, the synthetic nanoparticles are administered in an effective amount to induce or increase the activation of STING in a subject. As described herein, the STING signaling pathway in immune cells is a central mediator of innate immune response and when stimulated, induces expression of various interferons, cytokines and T cell recruitment factors that amplify and strengthen immune activity. Accordingly, in some embodiments, the activation of STING by the synthetic nanoparticles described herein, results in an induced or increased immune response.

In some embodiments, synthetic nanoparticles are administered as part of prophylactic vaccines or immunogenic compositions which confer resistance in a subject to subsequent exposure to infectious agents, or as part of therapeutic vaccines, which can be used to initiate or enhance a subject's immune response to a pre-existing antigen, such as a viral antigen in a subject infected with a virus or with cancer.

The desired outcome of a prophylactic or therapeutic immune response may vary according to the disease or condition to be treated, or according to ptinciples well known in the art. For example, an immune response against an infectious agent may completely prevent colonization and replication of an infectious agent, affecting "sterile immunity" and the absence of any disease symptoms. However, a vaccine against infectious agents may be considered effective if it reduces the number, severity or duration of symptoms; if it reduces the number of individuals in a population with symptoms; or reduces the transmission of an infectious agent. Similarly, immune responses against cancer, allergens or infectious agents may completely treat a disease, may alleviate symptoms, or may be one facet in an overall therapeutic intervention against a disease.

In some embodiments, the synthetic nanoparticles induce an improved effector cell response such as a CD4 T-cell immune response, against at least one of the component antigen(s) or antigenic compositions compared to the effector cell response obtained with the corresponding composition without the lipid conjugate. The term "improved effector cell response" refers to a higher effector cell response such as a CD8 or CD4 response obtained in a human patient after administration of the vaccine composition than that obtained after administration of the same composition without a lipid conjugate.

In some embodiments, the improved effector cell response is obtained in an immunologically unprimed patient, i.e. a patient who is seronegative to the antigen. This seronegativity may be the result of the patient having never faced the antigen (so-called "naïve" patient) or, alternatively, having failed to respond to the antigen once encountered. In some embodiments, the improved effector cell response is obtained in an immunocompromised subject.

In some embodiments, the improved effector cell response is assessed by measuring the number of cells producing any of the following cytokines: (1) cells producing at least two different cytokines (CD40L, IL-2, IFN-gamma, TNF-alpha); (2) cells producing at least CD40L and another cytokine (IL-2, TNF-alpha, IFN-gamma); (3) cells producing at least IL-2 and another cytokine (CD40L, TNF-alpha, IFN-gamma); (4) cells producing at least IFN-gamma and another cytokine (IL-2, TNF-alpha, CD40L); (5) and cells producing at least TNF-alpha and another cytokine (IL-2, CD40L, IFN-gamma).

An improved effector cell response is present when cells producing any of the above cytokines is in a higher amount following administration of the vaccine composition compared to control as discussed above.

In certain embodiments, the composition increases the number of T cells producing IFN-gamma, TNF-alpha, or a combination thereof, or increases the production of IFN-gamma, TNF-alpha, or a combination thereof in the existing T cells.

In some embodiments, the administration of the immunogenic composition alternatively or additionally induces an improved B-memory cell response in patients administered lipid conjugates compared to a control. An improved B-memory cell response is intended to mean an increased frequency of peripheral blood B lymphocytes capable of differentiation into antibody-secreting plasma cells upon antigen encounter as measured by stimulation of in vitro differentiation.

In a still another embodiment, the immunogenic composition increases the primary immune response as well as the CD8 response. The administration of the synthetic nanoparticles induces an improved CD4 T-cell, or CD8 T-cell immune response against a specific antigen compared to a control. This method may allow for inducing a CD4 T cell response which is more persistent in time.

Preferably the CD4 T-cell immune response, such as the improved CD4 T-cell immune response obtained in an unprimed subject, involves the induction of a cross-reactive CD4 T helper response. In particular, the amount of cross-reactive CD4 T cells is increased. The term "cross-reactive" CD4 response refers to CD4 T-cell targeting shared epitopes for example between influenza strains.

In some embodiments, the immunogenic compositions induce, increase or enhance an immune response to a specific antigen in a subject, In sonic embodiments, the immunogenic compositions induce, increase or enhance an antigen specific CD8+ T cell response in a subject.

Pharmaceutical Compositions and Modes of Administration

In certain embodiments, the disclosure provides for a pharmaceutical composition comprising a synthetic nanoparticle, a PNA-amphiphile and immunomodulatory compound, as described herein, with a pharmaceutically acceptable diluents, carrier, solubilizer, emulsifier, preservative and/or adjuvant. In certain embodiments, the disclosure provides for a pharmaceutical composition comprising a synthetic nanoparticle, a PNA-amphiphile and immunomodulatory compound, as described and an antigen, with a pharmaceutically acceptable diluents, carrier, solubilizer, emulsifier, preservative and/or adjuvant.

The disclosure provides synthetic nanoparticles, wherein the dissociation kinetics of the immunomodulatory compound from the PNA-amphiphile conjugate are considered slow (i.e., more than one day, more than two days, more than three days). Accordingly, in some aspects the pharmaceutical composition comprising the synthetic particles described herein, provide sustained release or sustained dosing of the immunomodulatory compound at or near the site of injection. In some aspects, the pharmaceutical composition has improved drug efficacy and safety relative to immunomodulatory compound administered alone.

In certain embodiments, acceptable formulation materials preferably are nontoxic to recipients at the dosages and concentrations employed. In certain embodiments, the formulation material(s) are for s.c. and/or I.V. administration. In certain embodiments, the pharmaceutical composition can contain formulation materials for modifying, maintaining or preserving, for example, the pH, osmolality, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company (1995). In certain embodiments, the formulation comprises PBS; 20 mM NaOAC, pH 5.2, 50 mM NaCl; and/or 10 mM NAOAC, pH 5.2, 9% Sucrose. In certain embodiments, the optimal pharmaceutical composition will be determined by one skilled in the art depending upon, for example, the intended route of administration, delivery format and desired dosage. See, for example, Remington's Pharmaceutical Sciences, supra. In certain embodiments, such compositions may influence the physical state, stability, rate of in vivo release and rate of in vivo clearance of an amphiphile and immunomodulatory compound, or nanoparticle, as described herein, with or without antigen.

In certain embodiments, the primary vehicle or carrier in a pharmaceutical composition can be either aqueous or non-aqueous in nature. For example, in certain embodiments, a suitable vehicle or carrier can be water for injection, physiological saline solution or artificial cerebrospinal fluid, possibly supplemented with other materials common in compositions for parenteral administration. In certain embodiments, the saline comprises isotonic phosphate-buffered saline. In certain embodiments, neutral buffered saline or saline mixed with serum albumin are further exemplary vehicles. In certain embodiments, pharmaceutical compositions comprise Tris buffer of about pH 7.0-8.5, or acetate buffer of about pH 4.0-5.5, which can further include sorbitol or a suitable substitute therefore. In certain embodiments, a composition comprising a synthetic nanoparticle, a PNA-amphiphile and immunomodulatory compound, as described herein, with or without antigen, can be prepared for storage by mixing the selected composition having the desired degree of purity with optional formulation agents (Remington's Pharmaceutical Sciences, supra) in the form of a lyophilized cake or an aqueous solution. Further, in certain embodiments, a composition comprising a synthetic nanoparticle, a PNA-amphiphile and immunomodulatory compound, as described herein, with or without antigen, can be formulated as a lyophilizate using appropriate excipients such as sucrose.

In certain embodiments, the pharmaceutical composition can be selected for parenteral delivery. In certain embodiments, the compositions can be selected for inhalation or for delivery through the digestive tract, such as orally. The preparation of such pharmaceutically acceptable compositions is within the ability of one skilled in the art.

In certain embodiments, the formulation components are present in concentrations that are acceptable to the site of administration. In certain embodiments, buffers are used to maintain the composition at physiological pH or at a slightly lower pH, typically within a pH range of from about 5 to about 8.

In certain embodiments, when parenteral administration is contemplated, a therapeutic composition can be in the form of a pyrogen-free, parenterally acceptable aqueous solution comprising an amphiphile and immunomodulatory compound, or nanoparticle described herein, with or without antigen, in a pharmaceutically acceptable vehicle. In certain embodiments, a vehicle for parenteral injection is sterile distilled water in which a synthetic nanoparticle, a PNA-amphiphile and immunomodulatory compound, as described herein, with or without antigen, is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that can provide for the controlled or sustained release of the product which can then be delivered via a depot injection. In certain embodiments, hyaluronic acid can also be used, and can have the effect of promoting sustained duration in the circulation. In certain embodiments, implantable drug delivery devices can be used to introduce the desired molecule.

In certain embodiments, a pharmaceutical composition can be formulated for inhalation. In certain embodiments, a synthetic nanoparticle, a PNA-amphiphile and immunomodulatory compound, as described herein, with or without antigen, can be formulated as a dry powder for inhalation. In certain embodiments, an inhalation solution comprising a synthetic nanoparticle, a PNA-amphiphile and immunomodulatory compound, as described herein, with or without antigen, can be formulated with a propellant for aerosol delivery. In certain embodiments, solutions can be nebulized. Pulmonary administration is further described in PCT application No. PCT/US94/001875, which describes pulmonary delivery of chemically modified proteins.

In certain embodiments, it is contemplated that formulations can be administered orally. In certain embodiments, a synthetic nanoparticle, a PNA-amphiphile and immunomodulatory compound, as described herein, with or without antigen, that is administered in this fashion can be formulated with or without those carriers customarily used in the compounding of solid dosage forms such as tablets and capsules. In certain embodiments, a capsule can be designed to release the active portion of the formulation at the point in the gastrointestinal tract when bioavailability is maximized and pre-systemic degradation is minimized. In certain embodiments, at least one additional agent can be included to facilitate absorption of a synthetic nanoparticle, a PNA-amphiphile and immunomodulatory compound, as described herein, with or without antigen. In certain embodiments, diluents, flavorings, low melting point waxes, vegetable oils, lubricants, suspending agents, tablet disintegrating agents, and binders can also be employed.

In certain embodiments, a pharmaceutical composition can involve an effective quantity of a synthetic nanoparticle, a PNA-amphiphile and immunomodulatory compound, as described herein, with or without antigen, in a mixture with non-toxic excipients which are suitable for the manufacture of tablets. In certain embodiments, by dissolving the tablets in sterile water, or another appropriate vehicle, solutions can be prepared in unit-dose form. In certain embodiments, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving a synthetic nanoparticle, a PNA-amphiphile and immunomodulatory compound, as described herein, with or without antigen, in sustained- or controlled-delivery formulations. In certain embodiments, techniques for formulating a variety of other sustained- or controlled-delivery means, such as liposome carriers, bio-erodible microparticles or porous beads and depot injections, are also known to those skilled in the art. See for example, PCT Application No. PCT/US93/00829 which describes the controlled release of porous polymeric microparticles for the delivery of pharmaceutical compositions. In certain embodiments, sustained-release preparations can include semipermeable polymer matrices in the form of shaped articles, e.g. films, or microcapsules. Sustained release matrices can include polyesters, hydrogels, polylactides (U.S. Pat. No. 3,773,919 and EP 058,481), copolymers of L-glutamic acid and gamma ethyl-L-glutamate (Sidman et al., Biopolymers, 22:547-556 (1983)), poly (2-hydroxyethyl-methacrylate) (Langer et al., J. Biomed. Mater. Res., 15: 167-277 (1981) and Langer, Chem. Tech., 12:98-105 (1982)), ethylene vinyl acetate (Langer et al., supra) or poly-D(−)-3-hydroxybutyric acid (EP 133,988). In certain embodiments, sustained release compositions can also include liposomes, which can be prepared by any of several methods known in the art. See, e.g., Eppstein et al, Proc. Natl. Acad. Sci. USA, 82:3688-3692 (1985); EP 036,676; EP 088,046 and EP 143,949.

The pharmaceutical composition to be used for in vivo administration typically is sterile. In certain embodiments, this can be accomplished by filtration through sterile filtration membranes. In certain embodiments, where the composition is lyophilized, sterilization using this method can be conducted either prior to or following lyophilization and reconstitution. In certain embodiments, the composition for parenteral administration can be stored in lyophilized form or in a solution. In certain embodiments, parenteral compositions generally are placed into a container having a sterile access port, for example, an intravenous solution bag or vial having a stopper pierceable by a hypodermic injection needle.

In certain embodiments, once the pharmaceutical composition has been formulated, it can be stored in sterile vials as a solution, suspension, gel, emulsion, solid, or as a dehydrated or lyophilized powder. In certain embodiments, such formulations can be stored either in a ready-to-use form or in a form (e.g., lyophilized) that is reconstituted prior to administration.

In certain embodiments, kits are provided for producing a single-dose administration unit. In certain embodiments, the kit can contain both a first container having a dried protein and a second container having an aqueous formulation. In certain embodiments, kits containing single and multi-chambered pre-filled syringes (e.g., liquid syringes and lyosyringes) are included.

In certain embodiments, the effective amount of a pharmaceutical composition comprising a synthetic nanoparticle, a PNA-amphiphile and immunomodulatory compound, as described herein, with or without antigen, to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which a synthetic nanoparticle, a PNA-amphiphile and immunomodulatory compound, as described herein, with or without antigen, are being used, the route of administration, and the diameter (body weight, body surface or organ diameter) and/or condition (the age and general health) of the patient. In certain embodiments, the clinician can titer the dosage and modify the route of administration to obtain the optimal therapeutic effect.

In certain embodiments, the frequency of dosing will take into account the pharmacokinetic parameters of a synthetic nanoparticle, a PNA-amphiphile and immunomodulatory compound, as described herein, with or without antigen, in the formulation used. In certain embodiments, a clinician will administer the composition until a dosage is reached that achieves the desired effect. In certain embodiments, the composition can therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. In certain embodiments, appropriate dosages can be ascertained through use of appropriate dose-response data.

In certain embodiments, the route of administration of the pharmaceutical composition is in accord with known methods, e.g. orally, through injection by intravenous, intraperitoneal, intracerebral (intra-parenchymal), intracerebroventricular, intramuscular, subcutaneously, intra-ocular, intraarterial, intraportal, or intralesional routes; by sustained release systems or by implantation devices. In certain embodiments, the compositions can be administered by bolus injection or continuously by infusion, or by implantation device. In certain embodiments, individual elements of the combination therapy may be administered by different routes.

In certain embodiments, the composition can be administered locally via implantation of a membrane, sponge or another appropriate material onto which the desired molecule has been absorbed or encapsulated. In certain embodiments, where an implantation device is used, the device can be implanted into any suitable tissue or organ, and delivery of the desired molecule can be via diffusion, timed-release bolus, or continuous administration. In certain embodiments, it can be desirable to use a pharmaceutical composition a synthetic nanoparticle, a PNA-amphiphile and immunomodulatory compound, as described herein, with or without antigen, in an ex vivo manner. In such instances, cells, tissues and/or organs that have been removed from the patient are exposed to a pharmaceutical composition comprising a synthetic nanoparticle, a PNA-amphiphile and immunomodulatory compound, as described herein, with or without antigen, after which the cells, tissues and/or organs are subsequently implanted back into the patient.

In certain embodiments, a synthetic nanoparticle, a PNA-amphiphile and immunomodulatory compound, as described herein, with or without antigen, can be delivered by implanting certain cells that have been genetically engineered, using methods such as those described herein, to express and secrete the polypeptides. In certain embodiments, such cells can be animal or human cells, and can be autologous, heterologous, or xenogeneic. In certain embodiments, the cells can be immortalized. In certain embodiments, in order to decrease the chance of an immunological response, the cells can be encapsulated to avoid infiltration of surrounding tissues. In certain embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

Kits

In certain embodiments, a kit can include a synthetic nanoparticle, a PNA-amphiphile and immunomodulatory compound, as described herein, with or without antigen, and instructions for use. The kits may comprise, in a suitable container, a synthetic nanoparticle, a PNA-amphiphile and immunomodulatory compound, as described herein, one or more controls, and various buffers, reagents, enzymes and other standard ingredients well known in the art. The container can include at least one vial, well, test tube, flask, bottle, syringe, or other container means, into which a synthetic nanoparticle, a PNA-amphiphile and immunomodulatory compound, as described herein may be placed, and in some instances, suitably aliquoted. Where an additional component is provided, the kit can contain additional containers into which this component may be placed. The kits can also include a means for containing a synthetic nanoparticle, a PNA-amphiphile and immunomodulatory compound, as described herein and any other reagent containers in close confinement for commercial sale. Such containers may include injection or blow-molded plastic containers into which the desired vials are retained. Containers and/or kits can include labeling with instructions for use and/or warnings.

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Materials and Methods

Peptide Nucleic Acid (PNA) Synthesis

The peptide nucleic acid (PNA) compounds were prepared manually using standard Fmoc-based solid phase peptide synthesis techniques on TentaGel® R (90 um) Rink-type resin (Peptides International). The PNA-G monomer was purchased from PNA Bio. For amphiphiles 1 and 2, where the diacyl tail was linked to the PNA segment through a carbamate, the tail linkage was formed on resin by reacting the deprotected N-terminus with 4 equivalents of N,N'-dihexadecanoyl-1,3-diaminopropane-2-(p-nitrophenyl)carbonate (1) (Sheikh, M.; Feig, J.; Gee, B.; Li, S.; Savva, M. Chemistry and Physics of Lipids 2003, 124, 49-61) or N,N'-dioctadecanoyl-1,3-diaminopropane-2-(p-nitrophenyl) carbonate (2), 0.1 equivalents of 4-(dimethylamino)pyridine, and 10 equivalents of N,N-diisopropylethylamine in a 7:3 mixture of dimethylformamide and dichloroethane at 65° C. for 2 hours. For amphiphiles 3-5, 8, and 9 with the tail linked through an amide bond, either 4-((1,3-dipalmitamidopropan-2-yl)oxy)-4-oxobutanoic acid (3,5) or 4-((1,3-distearamidopropan-2-yl)oxy)-4-oxobutanoic acid (4,8,9) was coupled to the deprotected N-terminus using standard peptide coupling conditions. The L-lysine-based diacyl tail found in amphiphiles 6 and 7 was prepared by coupling a terminal lysine residue with both amines deprotected with palmitic acid under standard peptide coupling conditions. After the peptide was capped with the hydrophobic tails, it was cleaved from the resin using 95% trifluoroacetic acid, 2.5% water, and 2.5% triisopropylsilane. The crude peptide was purified by reverse phase HPLC ($C_{18}$) using a mobile phase composed of acetonitrile and water with 0.1% by volume of trifluoroacetic acid. The identity of the product was confirmed by MALDI-tof MS and the concentration of stock solutions was measured by the UV absorbance at 260 nm using an extinction coefficient of 11.7 $mM^{-1}cm^{-1}$ for each guanine base. For example, an amphiphile containing three guanine bases would have an extinction coefficient of 35.1 $mM^{-1}cm^{-1}$.

Lipid Nanodisc Formulation

Lipid nanodiscs were prepared using the method reported by Johnson and Edwards (Biophysical J. 2003, 85 3839-3847) with minor modifications. Phospholipids were purchased from Avanti Polar Lipids. Two lipid compositions were explored. The first, referred to as disc type 1, contained 60 mol % hydrogenated soy L-α-phosphatidylcholine (HSPC), 20 mol % 1,2-distearoyl-sn-glycero-3-phosphoethanolamine-N-[methoxy(polyethylene glycol)-5000] ammonium (DSPE-PEG5000), and 20 mol % PNA amphiphile. The second composition, referred to as disc type 2, contained 40 mol % HSPC, 20 mol % DSPE-PEG5000, 20 mol % PNA amphiphile, and 20 mol % 1,2-dipalmitoyl-3-trimethylammonium-propane chloride (16:0 TAP). Lipid nanodiscs were formed by the thin-film hydration method followed by thermal annealing. Briefly, depending on the specific formulation, lipid stocks in either chloroform or ethanol were combined in a glass vial and the organic solvent was evaporated. The PNA amphiphile was added as an aqueous solution and evaporated under vacuum. The components were then completely solubilized in ethanol and the ethanol was removed by evaporation under a stream of nitrogen. The resulting film was further dried under high vacuum and then hydrated with water at 65° C. at a lipid concentration of 1.0 mg/mL for 20 minutes with frequent agitation. Subsequently, the solution was cooled to room temperature and then reheated to 65° C. for 20 minutes twice more. The resulting solution was filtered through a 0.2 μm syringe filter (Acrodisc® with Supor® membrane) and stored at 4° C. In order to load cdGMP onto the nanodisc, an aliquot of the nanodisc stock containing 1.5 molar equivalents of PNA amphiphile to cdGMP was combined with cdGMP in a buffer with 20 mM HEPES (pH 7) and 100 mM KCl at 10-times the dose intended for injection. This solution was heated to 65° C. for 5 minutes and then allowed to cool to room temperature over 10 minutes, with this heating and cooling cycle repeated twice more. The solution was then stored at 4° C. for a minimum of 18 hours before further dilution. Finally, solutions for injection were prepared by diluting the lipid nanodisc-cdGMP stock solution 10-fold into PBS buffer. These solutions were used within 1-2 hours or flash frozen and stored at −80° C.

PNA Nanofiber Aggregate Formation

In order to prepare PNA amphiphile-cdGMP nanofiber aggregates, PNA amphiphile and cdGMP were combined in pure water at a mole ratio of 1:1. Depending on the particular preparation, binding with the concentration of each component in the range of 0.5-1.0 mM was performed and similar results obtained. The solution was subsequently annealed at 60-65° C. for 10 minutes and then the appropriate volume of a 10× buffer stock was added to obtain a solution with 20 mM HEPES (pH 7) and 100 mM KCl. The solution was again annealed at 65° C. for 10 minutes and allowed to slowly to cool room temperature, left at room temperature for a minimum of 12 hours, and then stored at 4° C. for a minimum of 1 hour before pelleting the aggregate by spinning at 16000 g at 4° C. for 15 minutes. The supernatant was removed from the pellet and the pellet was resuspended in PBS. The cdGMP concentration of this aggregate stock was quantified by HPLC by comparing to a cdGMP standard curve. HPLC was performed using an analytical C18 column with a mobile phase containing acetonitrile and 0.1 M triethylamine acetate (TEAA) buffered water (pH 7) and by measuring the absorbance at 260 nm.

CDN Binding and Release Profile

The association of cdGMP with PNA nanofibers was quantified by measuring the amount of cdGMP bound by the aggregate when the PNA amphiphile concentration was held constant at 75 μM and the cdGMP concentration was increased (0, 2, 50, 75, 100, 150, 200 μM). The samples were prepared in PBS buffer and incubated for 18 hours at 37° C. The solutions were then centrifuged at 16000 g for 10 minutes and the supernatant was removed and the amount of unbound cdGMP was quantified by HPLC. The cdGMP concentration of this aggregate stock was quantified by HPLC by comparing to a cdGMP standard curve. HPLC was performed using an analytical C18 column with a mobile phase containing acetonitrile and 0.1 M triethylamine acetate (TEAA) buffered water (pH 7), and by measuring the absorbance at 260 nm.

Dynamic dialysis was used to gain insight on the rate of cdGMP release from both the nanofiber aggregates and the lipid nanodiscs. Samples (100 μL) containing PNA vehicles with cdGMP in PBS were loaded into dialysis tubes (Pur-A-Lyzer™ Mini Dialysis Kit, 12-14 kDa molecular weight cutoff) and placed in a bath containing 3.0 mL of PBS (in a 5 mL centrifuge tube), the tube was sealed, and then the sample was incubated at 37° C. At each time point, the complete volume of the bath was removed and the dialysis tube was placed into a new bath with 3.0 mL of PBS. For analysis, the bath volume was lyophilized to concentration the cdGMP and then redissolved with water at one-tenth the original volume and analyzed by HPLC (as describe above).

In Vitro STING Reporter Assay

In order to assay for the induction of STING signaling a mouse macrophage cell line (RAW-Lucia™ ISG cells, Invivogen) expressing a secreted Lucia luciferase under the transcriptional control of the ISG54 minimal promoter and IFN-stimulated response elements (ISRE) was used. The manufacturer's protocol was followed. Briefly, test solutions were prepared in PBS at 10-times the desired assay concentration and 20 μL was added to each assay well of a 96-well plate. Next, 100,000 RAW-ISG cells in 180 μL of complete DMEM media were added and the assay was incubated for 20 hrs. At this time, 10 μL aliquots of the cell supernatant were transferred to an opaque white 96-well plate and combined with 50 μL of Quanti-Luc (Invivogen) substrate and the luciferase activity was immediately measured by luminescence. Assays were performed with three technical replicates and experiments were repeated at least twice on different occasions with comparable results.

Animals

All procedures were performed under an IUCAC-approved animal protocol in accordance with the guidelines for animal care in a Massachusetts Institute of Technology animal facility inspected by the US Department of Agriculture.

Ovalbumin Vaccination

Female C57BL/6mice (6-12 week old, Jackson Laboratory) were immunized with 10 μg of ovalbumin antigen mixed with 5 μg of cyclic di-guanosine monophosphate (Invivogen) in 100 ml of sterile phosphate buffered saline containing 2 mM HEPES and 10 mM KCl. Solutions were administered by subcutaneous injection at the base of the tail. In the experimental group, the cdGMP was prebound to PNA amphiphile-containing nanodiscs by annealing in 20 mM HEPES (pH 7) 100 mM KCl at 65° C. for 5 minutes with cooling to 25° C. for 10 minutes for three cycles and then stored at 4° C. for 18 hours. Finally, the solution was diluted 10-fold into PBS buffer with ovalbumin for injection.

Flow Cytometry

The relative percentage of ovalbumin-specific CD8+ T cells in peripheral blood was quantified by staining with PE-H-2Kb OVA (SIINFEKL) tetramer (MBL International Corporation), CD8-APC (biolegend), and DAPI in PBS buffer supplemented with 1-wt % bovine serum albumin, 5 mM EDTA, and 50 nM dasatinib. Flow cytometric analysis was carried out using a BD LSR-II (BD Biosciences) instrument and analysis of cells was performed using FlowJo software (Tree Star Inc.).

Example 1

Generation of Synthetic Nanoparticles

Figure 1C:
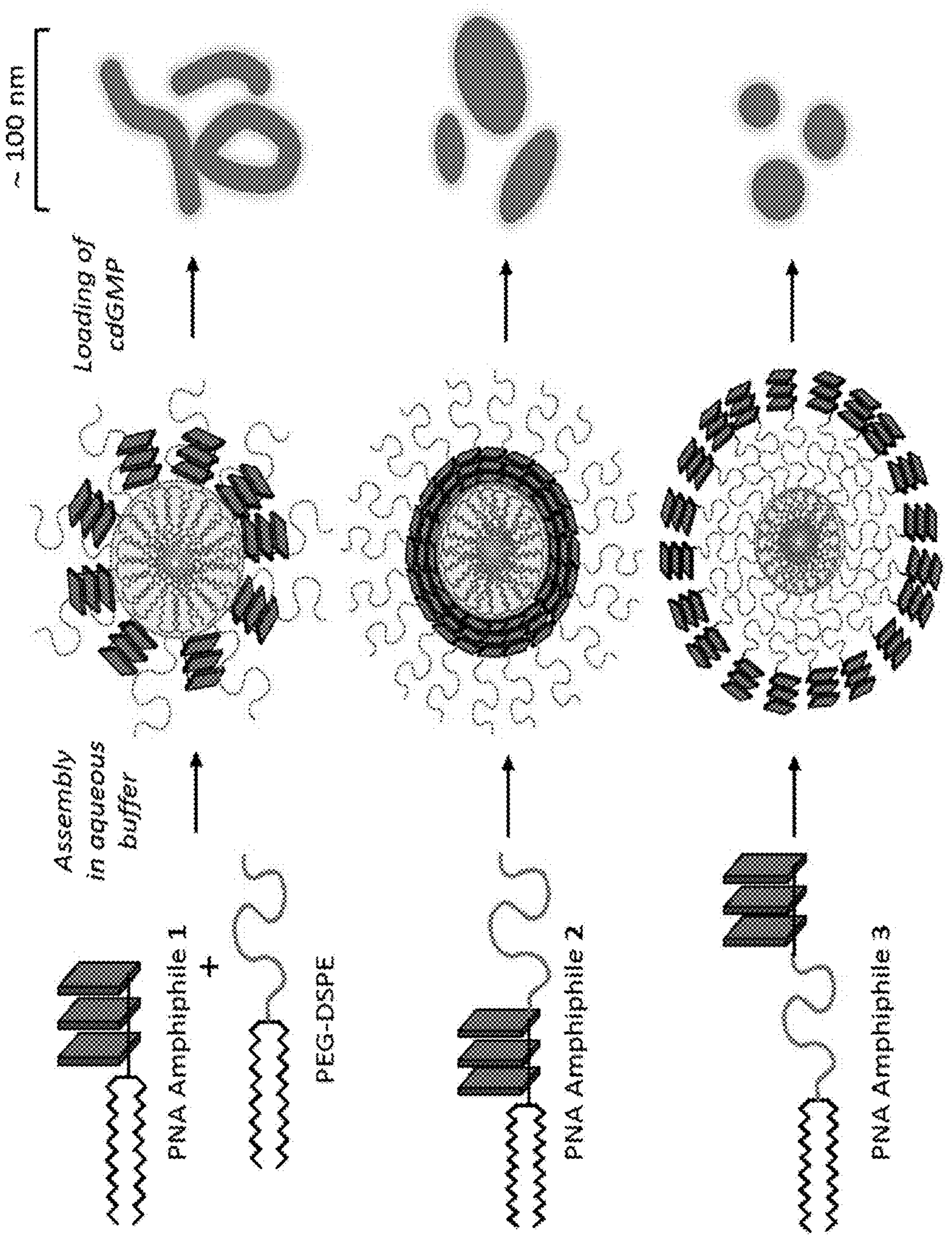
FIG. 1C depicts three exemplary configurations for an amphiphile containing a $G_3$-PNA headgroup and polyethylene glycol (PEG-DPSE) that are designed to noncovalently complex with an immunomodulatory compound, i.e., cdGMP. Schematics of the initial micellar structures formed by the PNA amphiphiles are shown in the middle column and the anticipated nanoparticles formed upon cdGMP complexation are shown in the right column.
Figure 2A:
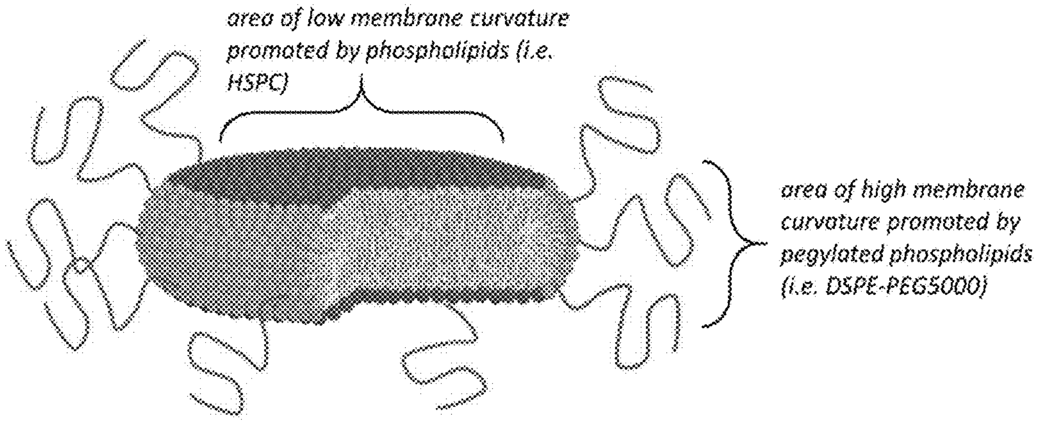
FIGS. 2A and 2B provide schematics of lipid nanodiscs without (FIG. 2A) or with (FIG. 2B) PNA amphiphiles (schematic was adapted from: E. Johansson et al. Biochimica et Biophysica Acta 1768 (2007) 1518-1525).
Figure 2B:
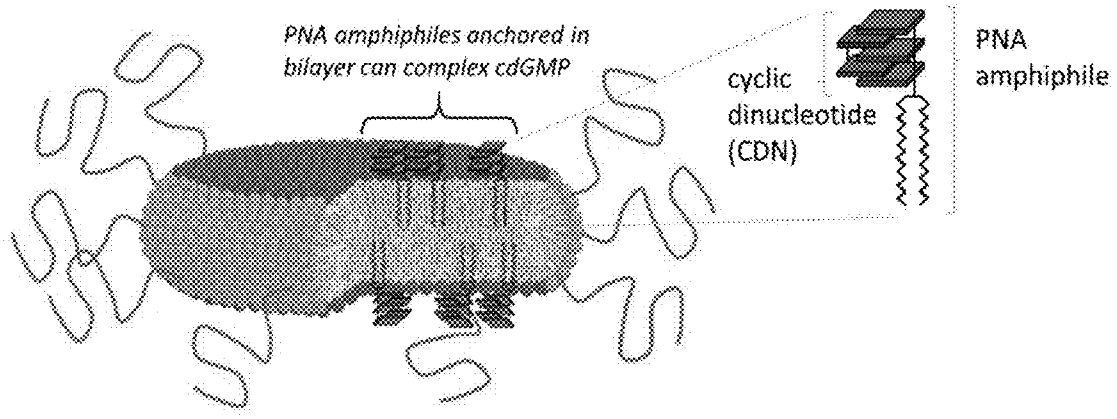

In this example, self-assembling amphiphiles capable of efficiently delivering an immunomodulatory compound (i.e., cyclic dinucleotide (CDN)), that incorporated peptide nucleic acid (PNA) were prepared. Upon the observation that cyclic di-guanine mono phosphate (cdGMP), a canonical immunostimulatory CDN, formed homodimers via pi-pi stacking, as shown in FIG. 1A, a PNA oligomer was analyzed for its potential to noncovalently bind cdGMP, as shown in FIG. 1B. A hydrophilic PNA oligomer with three guanine groups ($G_3$-PNA) and two lysines on either end (lysine-$G_3$-lysine) was added as a headgroup to a hydrophobic diacyl lipid tail, and tested for ability to reversibly bind cdGMP. Initial results showed that a population of the amphiphiles assembled into micelles, but upon mixing with cdGMP, precipitates formed. To prevent large-scale aggregation, polyethylene glycol (PEG), specifically PEG-DPSE, was utilized. FIG. 1C shows the different schematics of three exemplary amphiphiles containing $G_3$-PNA and PEG-DPSE, their resulting initial micellar structures and anticipated nanoparticles upon cdGMP loading. For example, the top amphiphile was generated by covalently conjugating $G_3$-PNA to one diacyl lipid tail and coformulating PEG-DSPE, and formed worm-like nanoparticles when combined with cdGMP. In contrast, the middle amphiphile was generated by covalently conjugating $G_3$-PNA to one diacyl lipid tail, and including a C-terminus cysteine to introduce a free thiol for conjugations of the maleimide-terminate PEG polymer, which formed micelles upon cdGMP loading. FIGS. 2A and 2B show schematics of lipid nanodiscs without (FIG. 2A; Johnsson and Edwards, *Biophysical J* 2003 3839) and with (FIG. 2B) PNA amphiphiles.

Figure 3:
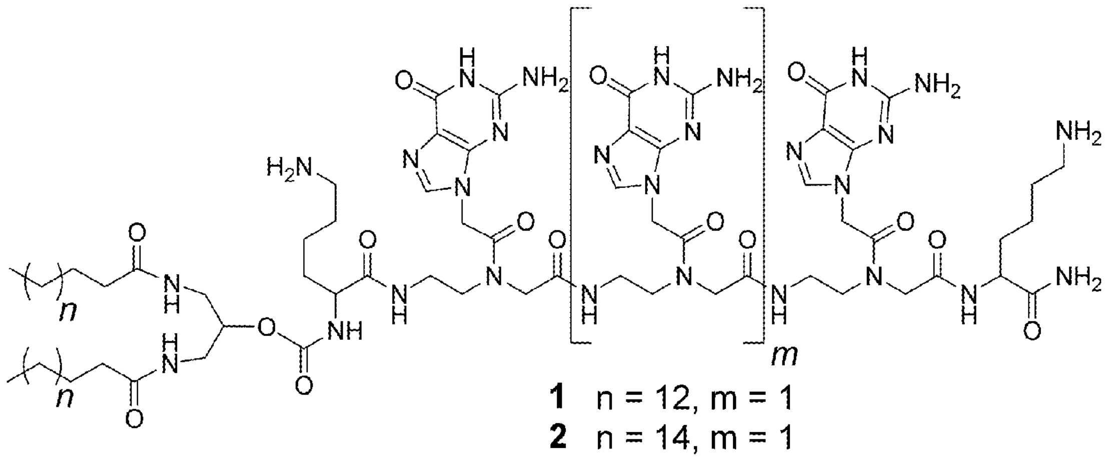
FIG. 3 shows the chemical structure of nine exemplary amphiphiles synthesized.
Figure 3:
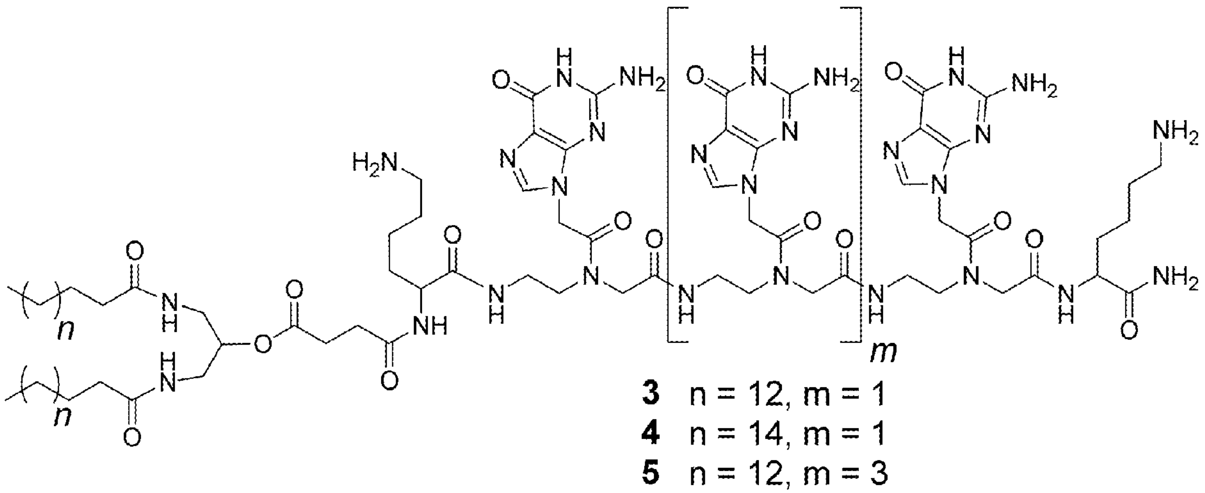
Figure 3:
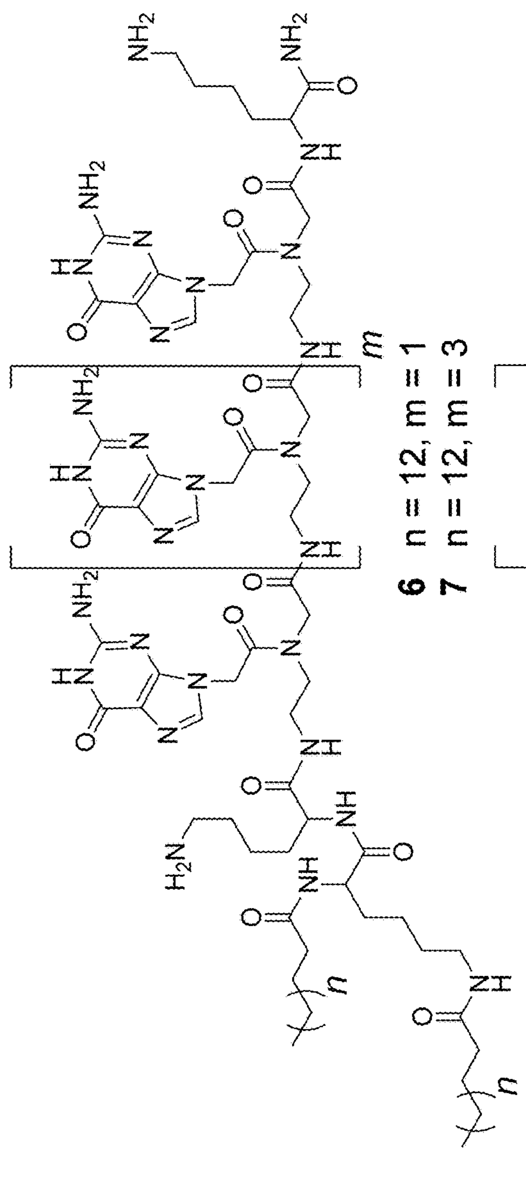
Figure 3:
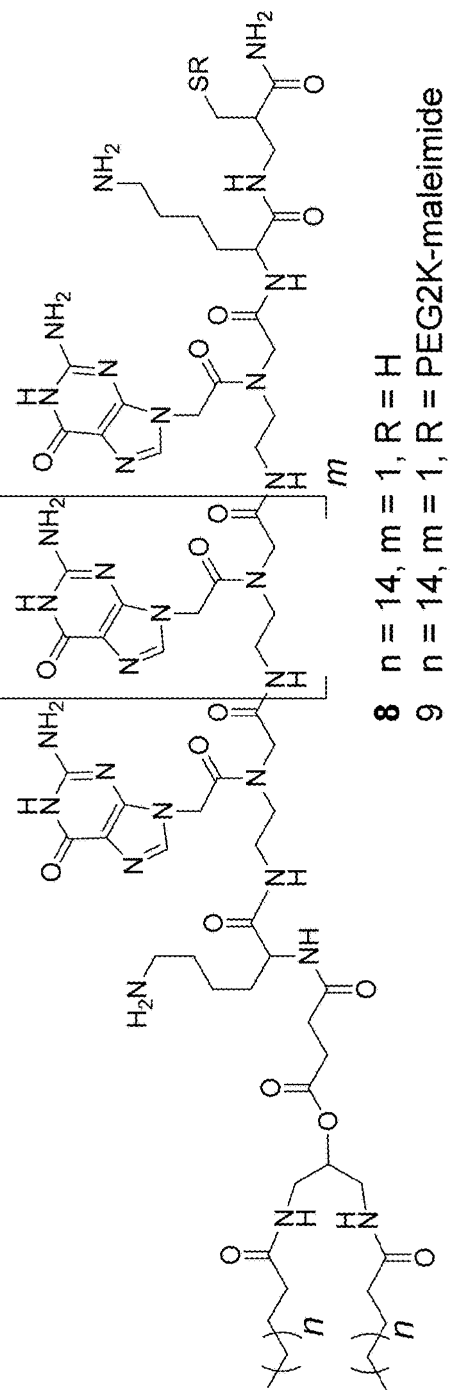

FIG. 3 shows the chemical structures of PNA Amphiphiles 1-9 generated as described above in Materials and Methods. The molecular mass of all nine amphiphiles generated was confirmed by MALDI-tof and is reported in the following table:

| PNA Amphiphile | MH+ expected | found |
|---|---|---|
| 1 | 1741 | 1742 |
| 2 | 1796 | 1796 |
| 3 | 1796 | 1795 |
| 4 | 1852 | 1852 |
| 5 | 2378 | 2378 |
| 6 | 1752 | 1753 |
| 7 | 2335 | 2336 |
| 8 | 1955 | 1955 |
| 9 | 4031 | 4030 |

Figure 4A:
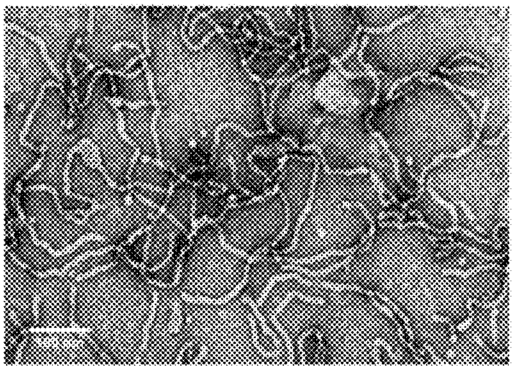
FIGS. 4A-4F provide images of nanostructures formed by PNA amphiphiles as characterized by transmission electron microscopy.
Figure 4B:
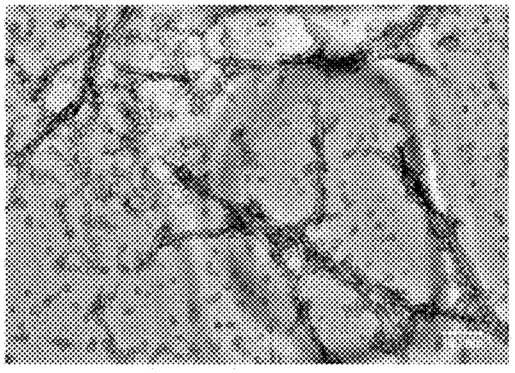
Figure 4C:
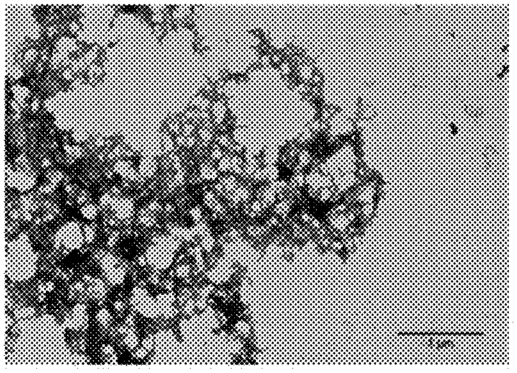
Figure 4D:
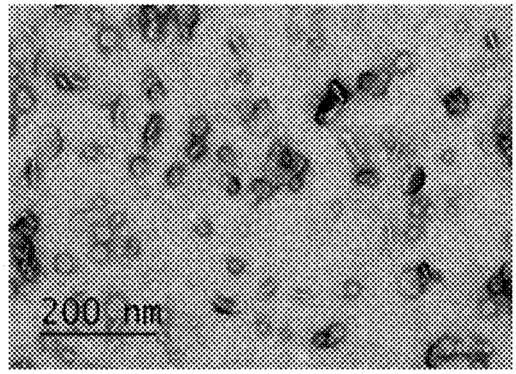
Figure 4E:
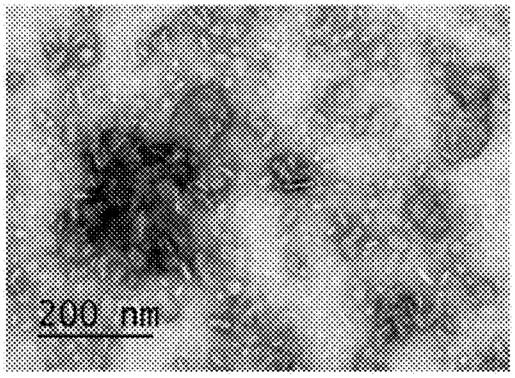
Figure 4F:
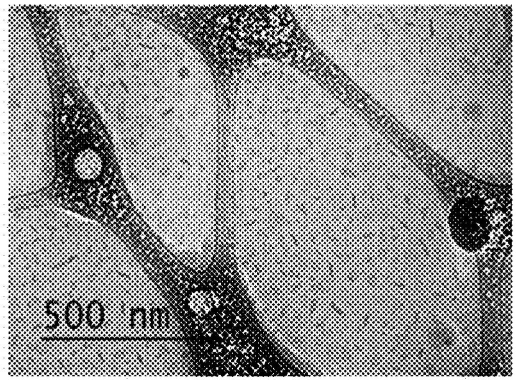

The nanostructures generated by the different amphiphiles were characterized by transmission electron microscopy. The results are shown in FIGS. 4A-4E. Specifically, FIG. 4A shows worm-like micelles prepared from 0.1 mM solution of PNA Amphiphile 2 in PBS buffer. FIG. 4B shows worm-like micelles prepared from a 0.1 mM solution of PNA Amphiphile 4 in PBS buffer. FIG. 4C shows aggregated structures prepared from a 0.1 mM solution of PNA Amphiphile 4 with 0.1 mM cdGMP in PBS buffer. FIG. 4D shows lipid nanodiscs containing PNA Amphiphile 3 (0.1 mM) in water. FIG. 4E shows lipid nanodiscs containing PNA Amphiphile 3 (0.1 mM) with cdGMP (0.1 mM) in water. FIG. 4F shows a hydrated cryopreserved sample without staining.

These results indicated PNA amphiphiles capable of carrying cyclic dinucleotides could be generated and formed various nanostructures.

Example 2

Analysis of Synthetic Nanoparticles

Figure 5A:
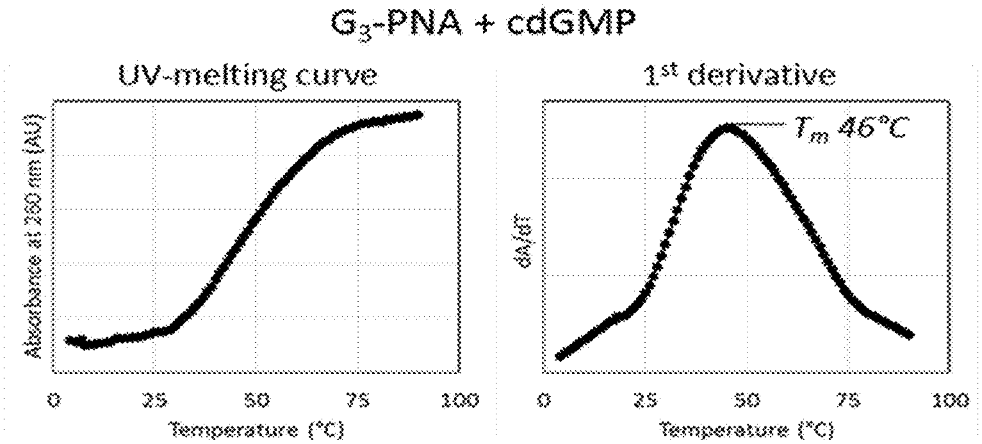
FIG. 5A is a UV-melting curve graph (left) and the first derivative of the UV-melting curve (right), confirming the association of cdGMP and $G_3$-PNA.
Figure 5B:
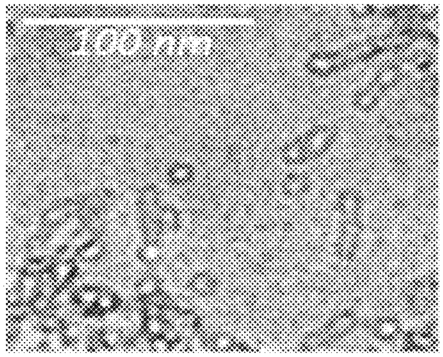
FIG. 5B is a representative image of cdGMP-complexed PNA micelles which formed small worm-like micelle structures.
Figure 6A:
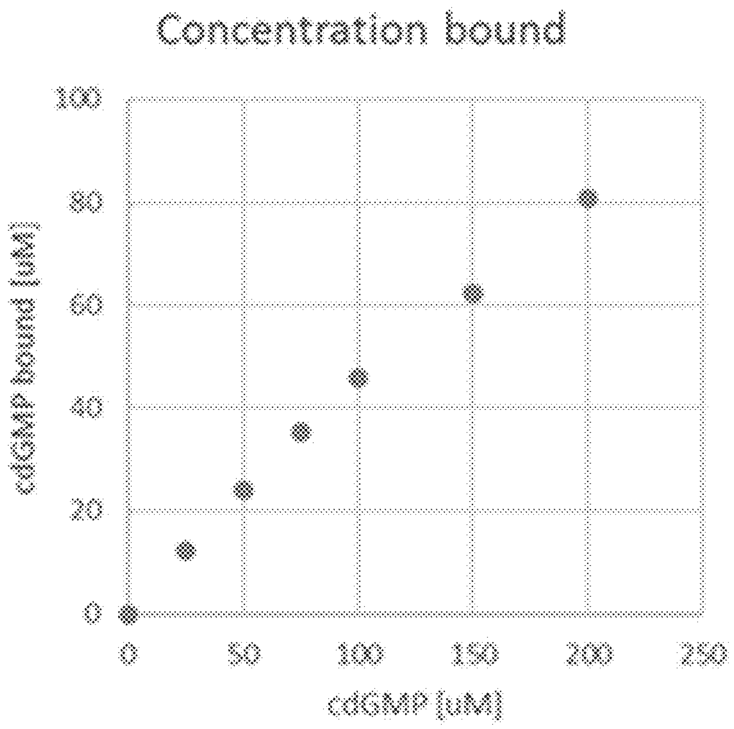
FIGS. 6A-6C are graphs showing the binding and release of cdGMP by PNA Amphiphile 1.
Figure 6B:
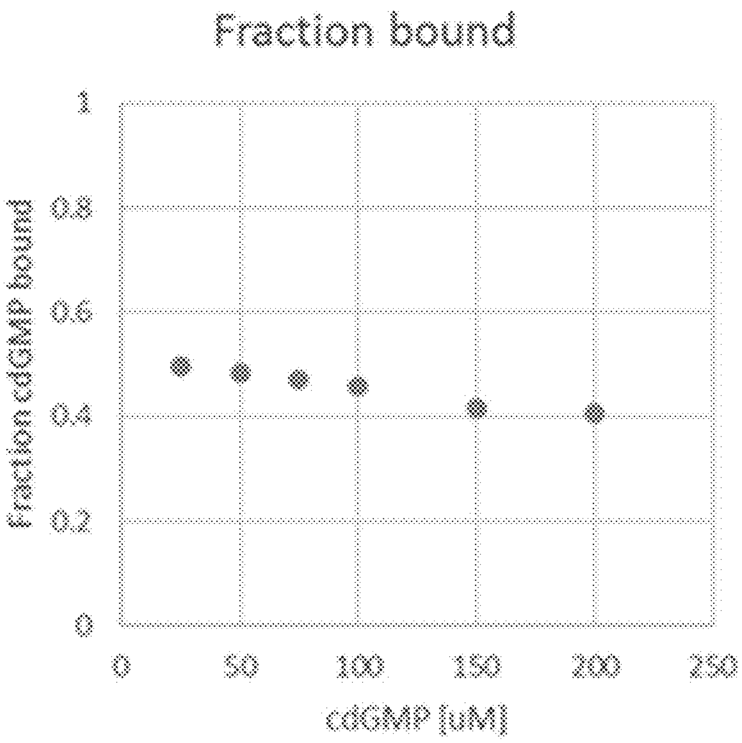
Figure 6C:
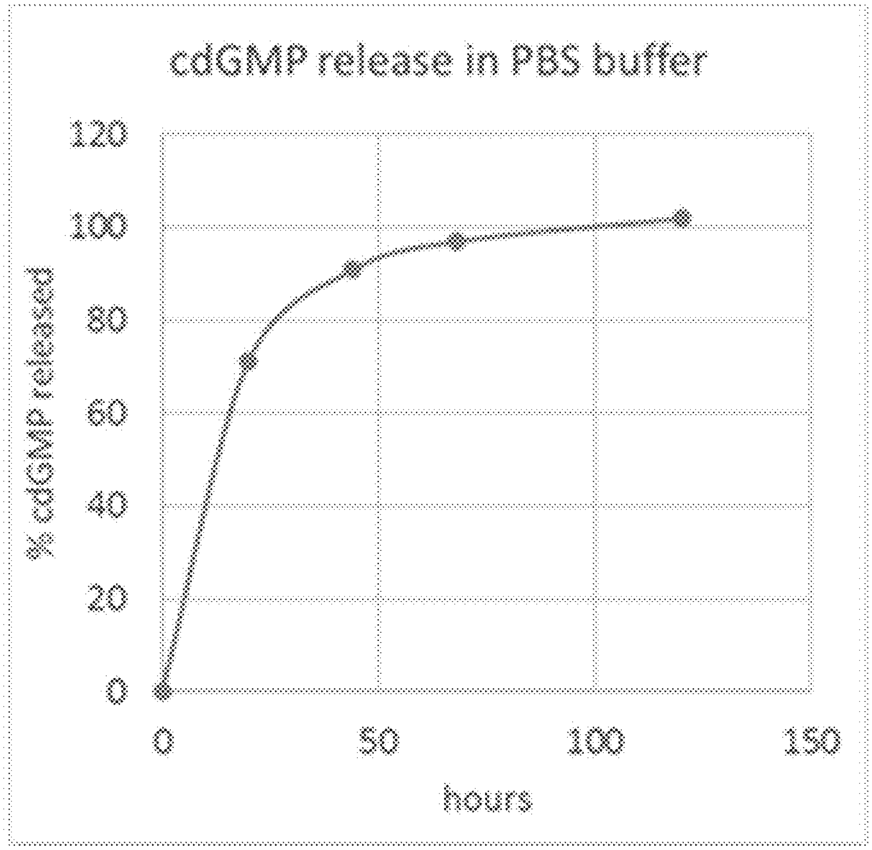

The synthetic nanoparticles generated in Example 1 were further analyzed. The association of cdGMP and $G_3$-PNA was confirmed by measuring the UV absorbance at 260 nm upon heating in PBS buffer. In polynucleic acids, such as DNA and RNA, base stacking results in a hypochromic shift that is lost upon dissociation of the complex. As shown in FIG. 5A, increasing guanine absorbance with heating, along with a single, broad transition with a $T_m$=46° C., was observed, consistent with the $G_3$-PNA-cdGMP complex. The nanostructure of self-assembled PNA Amphiphile 4 with cdGMP was confirmed through CryoEM, worm-like micelles resulted, as shown in FIG. 5B. The binding and release of cdGMP by PNA Amphiphile 1 was also tested. Results are shown in FIGS. 6A-6C. FIGS. 6A and 6B suggests that cdGMP incorporation into PNA amphiphile nanofiber aggregates was likely more complex than the initially envisioned 1:1 complex formation between a cdGMP molecule and a PNA amphiphile. The observation that increasing amounts of cdGMP resulted in increasing sequestration of cdGMP in the nanofiber aggregates without clear saturation behavior, as observed in FIG. 6A, suggested that in addition to cdGMP-PNA interactions, cdGMP-cdGMP noncovalent interactions may also play an important part in binding. FIG. 6C demonstrates that the rate of dissociation of the noncovalently-bound cdGMP from the nanofiber aggregates required more than 3 days to near completion. These slow dissociation kinetics indicate a sustained dosing of immunomodulatory compound at or near the site of injection, and thus provide improved drug efficacy and safety relative to the soluble CDN.

Next, the release profiles of PNA amphiphiles in lipid nanodiscs were determined. Two different types of lipid nanodiscs were evaluated, and are summarized in the table below.

| | Disc Type 1 | Disc Type 2 |
|---|---|---|
| High Tm Phospholipid (HSPC) | 60 mol % | 40 mol % |
| DSPE-PEG5000 | 20 mol % | 20 mol % |
| PNA Amphiphile | 20 mol % | 20 mol % |
| Cationic High Tm Lipid (16:0 TAP) | 0 mol % | 20 mol % |

Figure 7:
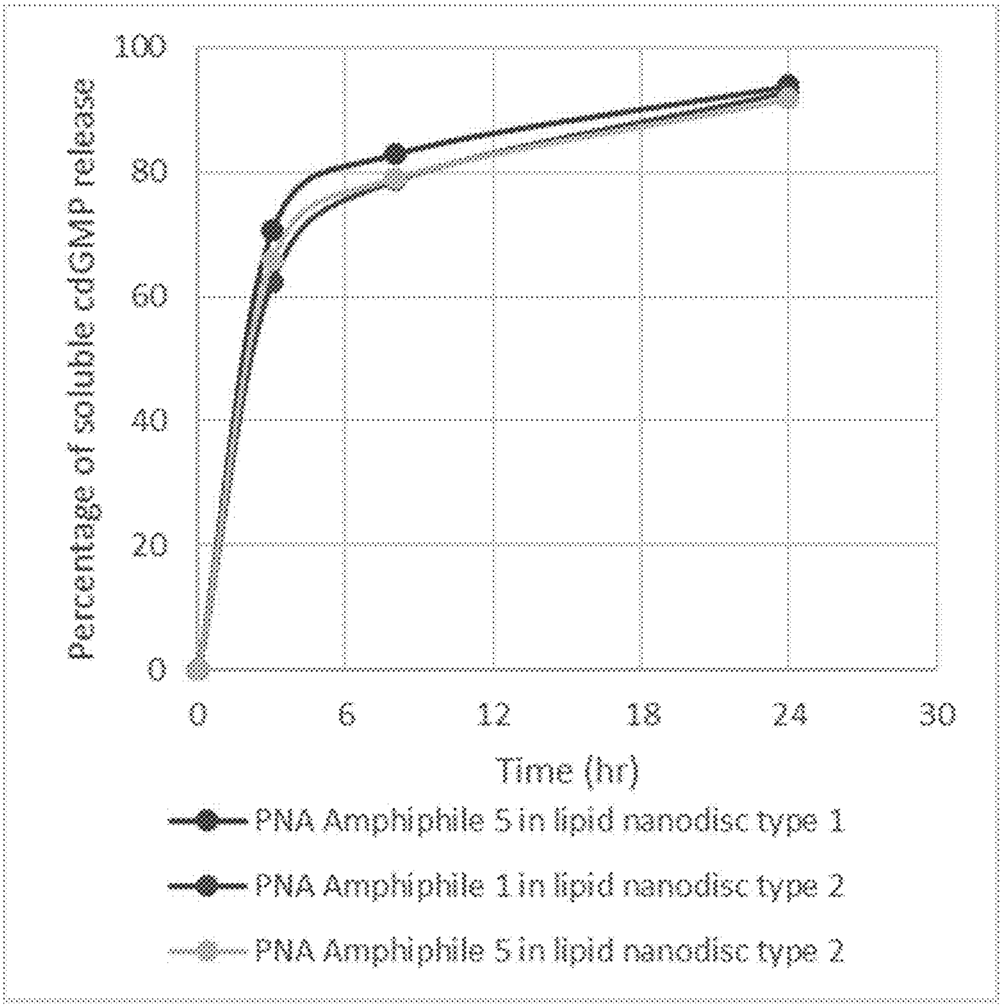
FIG. 7 is a graph showing the release profiles of PNA amphiphiles in lipid nanodiscs over time.

The release of cyclic dinucleotide from the lipid nanodiscs was measured by quantifying the amount of cdGMP released into a bath while samples were incubated in dialysis devices (12 kDa MWCO) at 37° C. in PBS. The results for PNA Amphiphiles 1 and 5 are shown in FIG. 7. As shown in FIG. 7, the release of cdGMP from PNA-amphiphile-containing lipid nanodisc occurred over the time span of approximately 24 hours. In the context of a vaccine delivered via intradermal, subcutaneous, or intramuscular injection, these results indicate a significant portion of the cdGMP will be released as the lipid nanodiscs traffic through the local lymphatic vessels to the draining lymph node. Relative to the administration of only cdGMP, which would be expected to rapidly drain into the vasculature due to its small size, more CDN will reach the lymphatics where a desired immune response can be achieved.

Since cdGMP is a canonical stimulator of STING, nanoparticles comprising the amphiphiles generated in Example 1 and cdGMP was tested for its ability to induce the STING signaling pathway. A STING reporter cell line (RAW macrophage cells expressing an interferon regulatory factor (IRF)-inducible secreted luciferase reporter), which expresses luciferase under the control of interferon-response genes activated by STING, was utilized.

Figure 8:
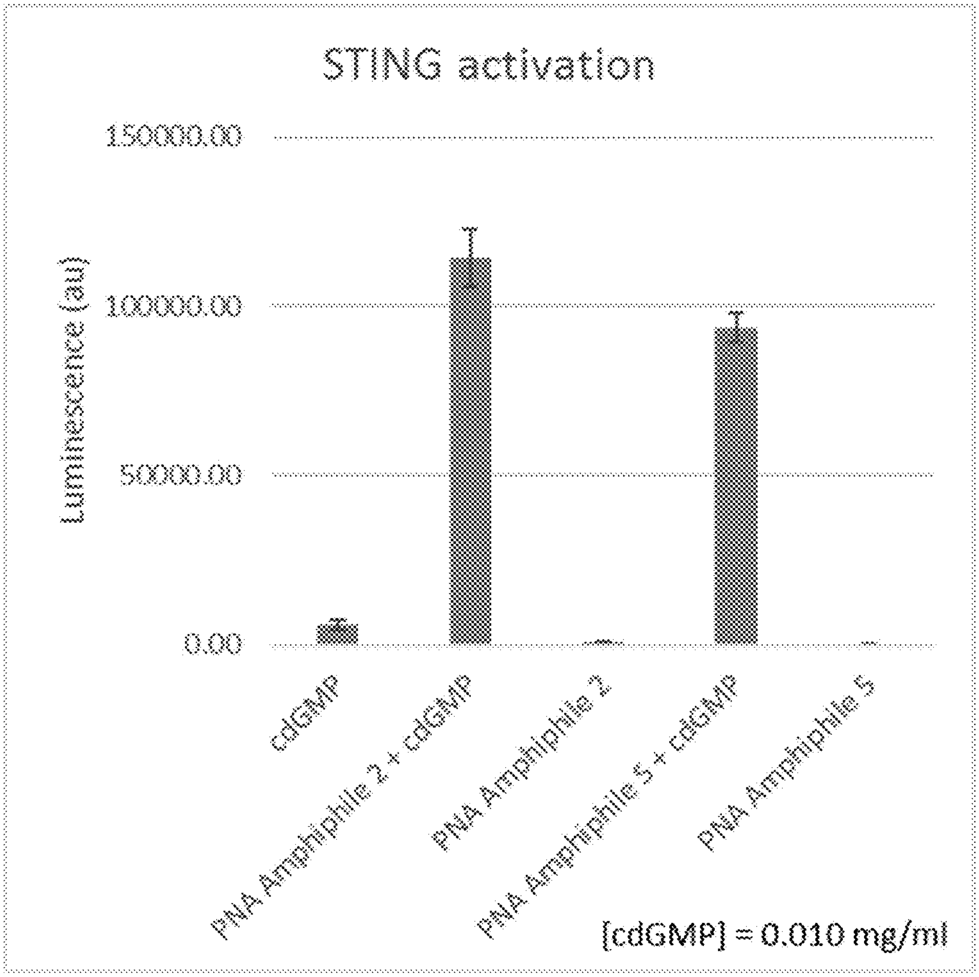
FIG. 8 is a graph showing an increase in in luminescence produced in a STING reporter cell line by aggregates carrying cdGMP using the Amphiphile 2 or 5 structure.

PNA Amphiphiles 2 and 5 were tested for their ability to activate STING in the reporter cell line. Specifically, PNA amphiphiles were premixed in the assay well to form aggregates and then the cells were added. FIG. 8 shows that nanoparticles carrying PNA Amphiphile 2 or Amphiphile 5 also activated STING more potently than an equivalent amount of free cdGMP or amphiphile alone. The increased activity of cdGMP when bound in aggregates was attributed, at least in part, to greater cellular uptake by the highly phagocytic RAW macrophages.

Figure 9:
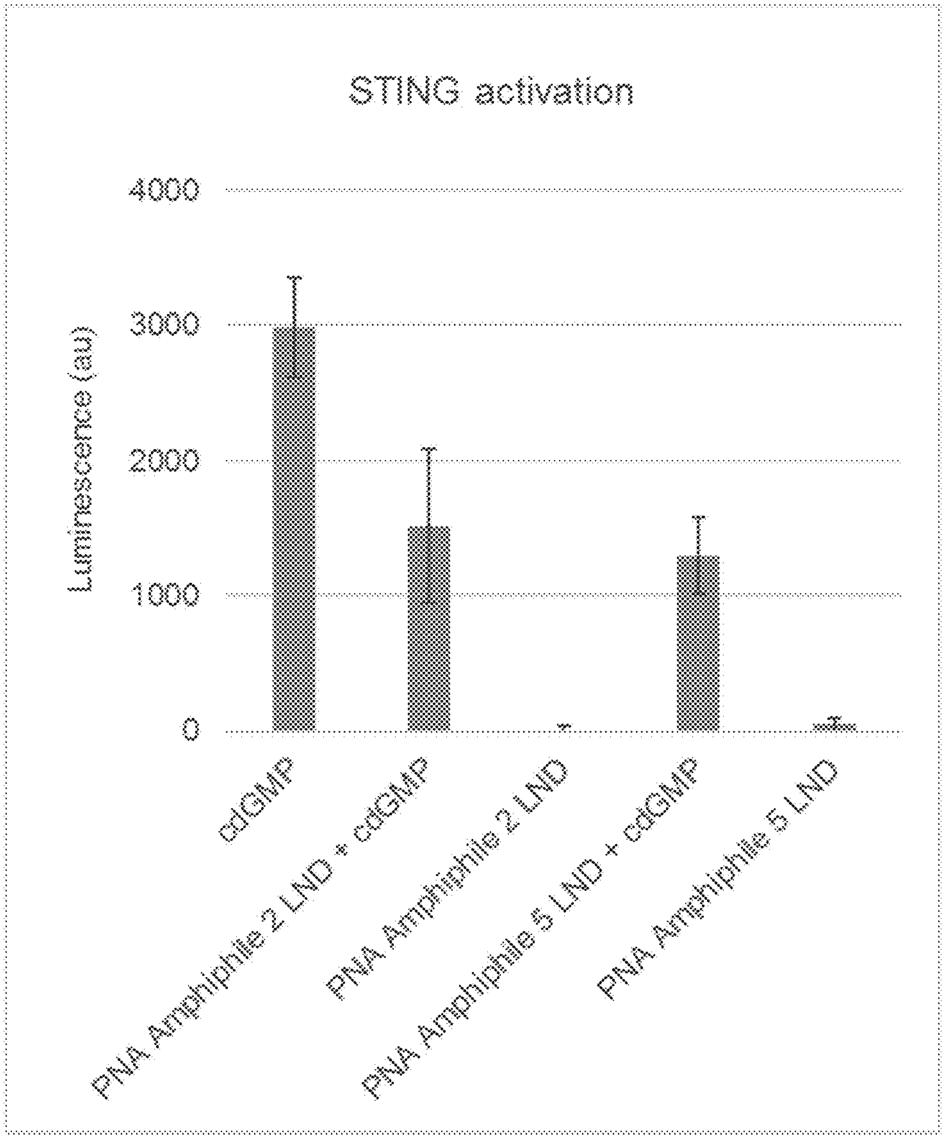
FIG. 9 is a graph showing an increase in luminescence produced in a STING reporter cell line by lipid nanodiscs (LND) carrying cdGMP using the Amphiphile 2 or 5 structure.

The ability of PNA amphiphile lipid nanodiscs to activate STING was also assessed. PNA amphiphile type 2 lipid nanodiscs loaded with cdGMP at a final cyclic dinucleotide concentration of 0.010 mg/mL were added to the STING reporter cell line and quantified after a 20 hour incubation period. Results are shown in FIG. 9. It was observed that lipid nanodisc bound cdGMP was less effective at inducing STING signaling in vitro in comparison to free cdGMP. In the context of an in vitro assay, this decreased stimulation was attributed to the lipid nanodiscs acting as competitive binders and thus lowering the overall amount of free cdGMP available to bind STING. Overall, these in vitro results indicated PNA amphiphiles were effective for promoting the activation of STING by CDNs.

Figure 10:
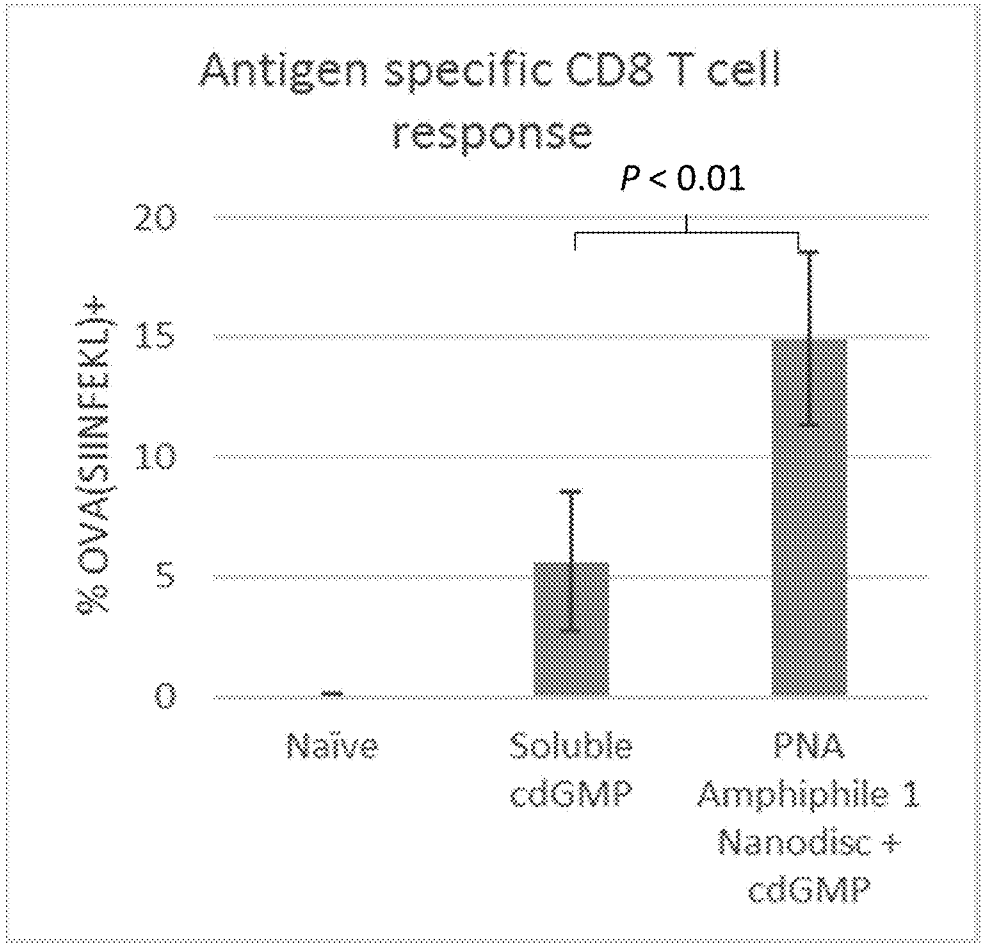
FIG. 10 is a graph showing the percentage of OVA (SIINFEKL)+CD8+ T cells in mice vaccinated with soluble cdGMP or lipid nanodiscs carrying cdGMP using the Amphiphile 1 structure, compared to naive mice.

Next, the in vivo activity of PNA amphiphiles in a vaccine was determined. C57BL/6J mice were immunized subcutaneously on days 0 and 14 with 0.01 mg of ovalbumin and 0.005 mg of cdGMP with or without complexation to PNA Amphiphile 1 lipid nanodiscs. On day 22, the percentage of antigen specific CD8+ T cells in peripheral blood was determined by flow cytometry using an ova-specific tetramer (SIINFEKL). FIG. 10 shows a significant increase in the antigen specific CD8+ T cell response in mice vaccinated with PNA Amphiphile 1 lipid nanodiscs loaded with cdGMP compared to cdGMP alone. These results indicated the usefulness of PNA amphiphiles to enhance an immune response to a specific antigen.

Equivalents

Those skilled in the art will recognize or be able to ascertain, using no more than routine experimentation, many equivalents of the specific embodiments described herein. Such equivalents are intended to be encompassed by the following claims.

We claim:

1. A synthetic nanoparticle comprising a PNA-amphiphile conjugate and an immunomodulatory compound, wherein the PNA-amphiphile conjugate comprises (i) a peptide nucleic acid (PNA) oligomer comprising at least one guanine nucleoside, or an analog thereof, (ii) one or more lipids, and optionally, (iii) a polymer, wherein the immunomodulatory compound is a cyclic dinucleotide (CDN), and wherein the CDN is noncovalently complexed with the PNA oligomer, thereby forming a synthetic nanoparticle.

2. The synthetic nanoparticle of claim 1, wherein the PNA oligomer comprises 3 guanine nucleosides, or analogs thereof, or at least one positively charged amino acid.

3. The synthetic nanoparticle of claim 1, wherein the positively charged amino acid is lysine or arginine.

4. The synthetic nanoparticle of claim 1, wherein the PNA oligomer is represented from N- to C- terminus by the formula: $Xaa_1$-$(G)_n$-$Xaa_2$, wherein $Xaa_1$ is selected from the group consisting of lysine and arginine, wherein G is guanine and n is 1 to 12, and wherein $Xaa_2$ is selected from the group consisting of lysine and arginine.

5. The synthetic nanoparticle of claim 4, wherein $Xaa_1$ and $Xaa_2$ are lysine and n is 3 to 6.

6. The synthetic nanoparticle of claim 1, wherein the PNA oligomer is lysine-$(G)_3$-lysine, wherein G is guanine.

7. The synthetic nanoparticle of claim 1, wherein the one or more lipids is a diacyl lipid tail.

8. The synthetic nanoparticle of claim 1, wherein the CDN is cyclic di-guanine mono phosphate (cdGMP), an agonist of STING (STimulator of Interferon Genes), cyclic di-inosine monophosphate, or cyclic d-AMP.

9. The synthetic nanoparticle of claim 1, further comprising a polymer, wherein the polymer is polyethylene glycol, or another hydrophilic polymer.

10. The synthetic nanoparticle of claim 1, wherein the nanoparticle has a diameter in the range of approximately 10 nm to approximately 100 nm.

11. The synthetic nanoparticle of claim 1, wherein the nanoparticle comprises a structure selected from the group consisting of a worm-like micelle, a disc-like micelle, a nanofiber and a spherical micelle.

12. A composition comprising a synthetic nanoparticle of claim 1, and a pharmaceutically acceptable carrier.

13. A method of modulating an immune response in a subject, inducing or enhancing an immune response in a subject with cancer, or treating cancer, comprising administering to a subject in need thereof the composition of claim 12.

14. A vaccine comprising the synthetic nanoparticle of claim 1, and an antigen, optionally wherein the antigen is conjugated to the synthetic nanoparticle.

15. A method of immunizing a subject comprising administering the vaccine of claim 14.

16. A complex comprising a peptide nucleic acid (PNA) oligomer comprising at least one guanine nucleoside, or an analog thereof, noncovalently bound to a cyclic dinucleotide (CDN).

17. A PNA-amphiphile conjugate comprising a peptide nucleic acid (PNA) oligomer comprising at least one guanine nucleoside, or an analog thereof, and one or more lipids, and optionally, a polymer conjugated to the one or more lipids or the PNA.

18. A method of making a synthetic nanoparticle comprising combining the PNA-amphiphile conjugate of claim 17 with a cyclic dinucleotide (CDN), thereby forming a synthetic nanoparticle.

19. A method of inducing an antigen specific CD8+T cell response in a subject inducing an immune response to an antigen in a subject, or activating STING in a subject, the method comprising administering the vaccine of claim 14 to the subject.

* * * * *

UNITED STATES PATENT AND TRADEMARK OFFICE

CERTIFICATE OF CORRECTION

PATENT NO. : 10,300,145 B2
APPLICATION NO. : 15/650177
DATED : May 28, 2019
INVENTOR(S) : Irvine et al.

It is certified that error appears in the above-identified patent and that said Letters Patent is hereby corrected as shown below:

In the Specification

In Column 1, Lines 11-13, delete:
“This invention was made with Government support under Grant No. R01 EB004866 awarded by National Institutes of Health. The Government has certain rights in the invention.”

And insert:
-- This invention was made with government support under R01 CA174795 and R01 EB004866 awarded by the National Institutes of Health. The government has certain rights in the invention. --

Signed and Sealed this
Ninth Day of December, 2025

John A. Squires
*Director of the United States Patent and Trademark Office*